(12) United States Patent
Diduch et al.

(10) Patent No.: US 10,709,488 B2
(45) Date of Patent: Jul. 14, 2020

(54) BICEPS TENODESIS DELIVERY TOOLS

(71) Applicant: Medos International Sarl, Le Locle (CH)

(72) Inventors: David R. Diduch, Charlottesville, VA (US); Mark H. Getelman, Tarzana, CA (US); Jacob A. Marks, Foxboro, MA (US); Gerome Miller, Randolph, MA (US); Matthew J. Ravenscroft, Mere (GB); Mehmet Z. Sengun, Canton, MA (US); Howard C. Tang, Boston, MA (US)

(73) Assignee: MEDOS INTERNATIONAL SÁRL, Le Locle (CH)

( * ) Notice: Subject to any disclaimer, the term of this patent is extended or adjusted under 35 U.S.C. 154(b) by 4 days.

(21) Appl. No.: 16/047,650

(22) Filed: Jul. 27, 2018

(65) Prior Publication Data

US 2018/0344376 A1    Dec. 6, 2018

Related U.S. Application Data

(62) Division of application No. 14/610,730, filed on Jan. 30, 2015, now Pat. No. 10,076,374.

(60) Provisional application No. 62/067,701, filed on Oct. 23, 2014.

(51) Int. Cl.
*A61B 17/88*    (2006.01)
(52) U.S. Cl.
CPC .................................. *A61B 17/88* (2013.01)
(58) Field of Classification Search
CPC .............. A61B 17/888; A61B 17/8883; A61B 17/8886; A61B 17/8888; A61B 17/8891; A61B 2017/0409

USPC ......................................................... 606/104
See application file for complete search history.

(56) References Cited

U.S. PATENT DOCUMENTS

| | | | |
|---|---|---|---|
| 651,949 A | 6/1900 | Lillie |
| 775,427 A | 11/1904 | Lusted |
| 1,426,320 A | 8/1922 | Reid |
| 1,925,385 A | 9/1933 | Humes et al. |
| 2,243,717 A | 5/1941 | Godoy |
| 2,288,584 A | 6/1942 | Longfellow |
| 2,381,050 A | 8/1945 | Hardinge |
| 2,484,655 A | 10/1949 | Shreve |
| 3,073,189 A | 1/1963 | Paige |
| 3,089,359 A | 5/1963 | Poulin |
| 3,103,926 A | 9/1963 | Cochran et al. |
| 3,130,763 A | 4/1964 | Bernard et al. |

(Continued)

FOREIGN PATENT DOCUMENTS

| AU | 2013201310 B2 | 5/2015 |
|---|---|---|
| CN | 1378439 A | 11/2002 |

(Continued)

OTHER PUBLICATIONS

European Search Report for EP Application No. 15191001.5, dated Apr. 1, 2016. (7 pages).

(Continued)

*Primary Examiner* — Eric S Gibson

(57) ABSTRACT

Methods and devices are provided for anchoring a ligament or tendon to bone. In particular, various delivery tools, including a variety of sheath inserter tools, are provided. The tools can be used to position a tendon within a prepared bone hole, and to deliver a sheath into the bone hole.

8 Claims, 25 Drawing Sheets

(56) References Cited

U.S. PATENT DOCUMENTS

| | | |
|---|---|---|
| 3,298,410 A | 1/1967 | Noboru |
| 4,503,737 A | 3/1985 | DiGiovanni |
| 4,512,344 A * | 4/1985 | Barber ............ A61B 17/32002 |
| | | 600/568 |
| 4,592,346 A | 6/1986 | Jurgutis |
| 4,640,271 A | 2/1987 | Lower |
| 4,641,640 A * | 2/1987 | Griggs ................ A61B 17/746 |
| | | 606/66 |
| 4,687,392 A | 8/1987 | Bidwell |
| 4,704,055 A | 11/1987 | Guhring |
| 4,711,232 A | 12/1987 | Fischer et al. |
| 4,773,417 A | 9/1988 | Moore et al. |
| 4,851,005 A | 7/1989 | Hunt et al. |
| 4,858,810 A | 8/1989 | Intlekofer et al. |
| 4,871,289 A | 10/1989 | Choiniere |
| 4,901,717 A | 2/1990 | Moore et al. |
| 4,919,130 A | 4/1990 | Stoy et al. |
| 4,921,383 A | 5/1990 | Fischer |
| 4,950,270 A | 8/1990 | Bowman et al. |
| 4,960,420 A | 10/1990 | Goble et al. |
| 4,976,715 A | 12/1990 | Bays et al. |
| 4,988,351 A | 1/1991 | Paulos et al. |
| 5,026,376 A | 6/1991 | Greenberg |
| 5,029,573 A | 7/1991 | Chow |
| 5,105,690 A | 4/1992 | Lazzara et al. |
| 5,116,337 A | 5/1992 | Johnson |
| 5,129,906 A | 7/1992 | Ross et al. |
| 5,180,384 A | 1/1993 | Mikhail |
| 5,209,756 A | 5/1993 | Seedhom et al. |
| 5,211,647 A | 5/1993 | Schmieding |
| 5,226,714 A | 7/1993 | Wright |
| 5,226,890 A | 7/1993 | Ianniruberto et al. |
| 5,234,435 A | 8/1993 | Seagrave, Jr. |
| 5,236,445 A | 8/1993 | Hayhurst et al. |
| 5,242,418 A | 9/1993 | Weinstein |
| 5,258,012 A | 11/1993 | Luscombe et al. |
| 5,266,075 A | 11/1993 | Clark et al. |
| 5,273,024 A | 12/1993 | Menon et al. |
| 5,290,296 A | 3/1994 | Phillips |
| 5,290,297 A | 3/1994 | Phillips |
| 5,314,427 A | 5/1994 | Goble et al. |
| 5,320,626 A | 6/1994 | Schmieding |
| 5,325,868 A | 7/1994 | Kimmelstiel |
| 5,325,883 A | 7/1994 | Orr |
| 5,352,229 A | 10/1994 | Goble et al. |
| 5,352,231 A | 10/1994 | Brumfield et al. |
| 5,380,334 A | 1/1995 | Torrie et al. |
| 5,383,878 A | 1/1995 | Roger et al. |
| 5,385,541 A | 1/1995 | Kirsch et al. |
| 5,409,493 A | 4/1995 | Greenberg |
| 5,425,490 A | 6/1995 | Goble et al. |
| 5,425,733 A | 6/1995 | Schmieding |
| 5,445,642 A | 8/1995 | McNulty et al. |
| 5,454,811 A | 10/1995 | Huebner |
| 5,456,721 A | 10/1995 | Legrand |
| 5,478,329 A | 12/1995 | Ternamian |
| 5,505,735 A | 4/1996 | Li |
| 5,527,341 A | 6/1996 | Gogolewski et al. |
| 5,571,104 A | 11/1996 | Li |
| 5,601,558 A | 2/1997 | Torrie et al. |
| 5,601,562 A | 2/1997 | Wolf et al. |
| 5,607,432 A | 3/1997 | Fucci |
| 5,630,805 A | 5/1997 | Ternamian |
| 5,632,748 A | 5/1997 | Beck, Jr. et al. |
| 5,651,790 A | 7/1997 | Resnick et al. |
| 5,653,763 A | 8/1997 | Errico et al. |
| 5,655,330 A | 8/1997 | Parsons, III |
| 5,658,289 A | 8/1997 | Boucher et al. |
| 5,660,186 A | 8/1997 | Bachir |
| 5,662,655 A | 9/1997 | Laboureau et al. |
| 5,662,657 A | 9/1997 | Carn |
| 5,669,925 A | 9/1997 | Saunders |
| 5,676,499 A | 10/1997 | Tukala |
| D388,171 S | 12/1997 | Fekete |
| 5,700,266 A | 12/1997 | Harryman, II |
| 5,702,398 A | 12/1997 | Tarabishy |
| 5,713,903 A | 2/1998 | Sander et al. |
| 5,720,753 A | 2/1998 | Sander et al. |
| 5,738,666 A | 4/1998 | Watson et al. |
| 5,746,743 A | 5/1998 | Greenberg |
| 5,779,707 A | 7/1998 | Bertholet et al. |
| 5,782,865 A | 7/1998 | Grotz |
| RE36,020 E | 12/1998 | Moore et al. |
| 5,895,351 A | 4/1999 | Nottage et al. |
| 5,897,565 A | 4/1999 | Foster |
| 5,899,906 A | 5/1999 | Schenk |
| 5,899,938 A | 5/1999 | Sklar et al. |
| 5,904,685 A | 5/1999 | Walawalkar |
| 5,906,632 A | 5/1999 | Bolton |
| 5,941,882 A * | 8/1999 | Jammet ................ A61B 17/04 |
| | | 606/232 |
| 5,948,000 A | 9/1999 | Larsen et al. |
| 5,948,001 A * | 9/1999 | Larsen ............... A61B 17/0469 |
| | | 606/104 |
| 5,957,953 A | 9/1999 | DiPoto et al. |
| 5,961,520 A | 10/1999 | Beck, Jr. et al. |
| 5,961,521 A | 10/1999 | Roger |
| 5,968,078 A | 10/1999 | Grotz |
| 5,993,458 A | 11/1999 | Vaitekunas et al. |
| 6,024,758 A | 2/2000 | Thal |
| 6,027,523 A | 2/2000 | Schmieding |
| 6,077,267 A | 6/2000 | Huene |
| 6,117,139 A | 9/2000 | Shino |
| 6,123,711 A | 9/2000 | Winters |
| 6,143,016 A | 11/2000 | Bleam et al. |
| 6,143,017 A | 11/2000 | Thal |
| 6,221,107 B1 | 4/2001 | Steiner et al. |
| 6,231,606 B1 | 5/2001 | Graf et al. |
| 6,251,119 B1 | 6/2001 | Addis |
| 6,270,518 B1 | 8/2001 | Pedlick et al. |
| D448,482 S | 9/2001 | Bellofatto et al. |
| 6,283,948 B1 | 9/2001 | McKernan et al. |
| 6,306,138 B1 | 10/2001 | Clark et al. |
| 6,319,270 B1 | 11/2001 | Grafton et al. |
| 6,325,805 B1 | 12/2001 | Ogilvie et al. |
| 6,379,361 B1 | 4/2002 | Beck, Jr. et al. |
| 6,405,863 B1 | 6/2002 | Dhindsa |
| 6,443,956 B1 | 9/2002 | Ray |
| 6,464,706 B1 | 10/2002 | Winters |
| 6,517,519 B1 | 2/2003 | Rosen et al. |
| 6,517,564 B1 | 2/2003 | Grafton et al. |
| 6,533,816 B2 | 3/2003 | Sklar |
| 6,544,281 B2 | 4/2003 | ElAttrache et al. |
| 6,554,862 B2 | 4/2003 | Hays et al. |
| 6,558,389 B2 | 5/2003 | Clark et al. |
| 6,562,044 B1 | 5/2003 | Cooper |
| 6,579,295 B1 | 6/2003 | Supinski |
| 6,592,587 B1 | 7/2003 | Roger |
| 6,599,290 B2 | 7/2003 | Bailey et al. |
| 6,613,065 B2 | 9/2003 | Lajtai |
| 6,632,245 B2 | 10/2003 | Kim |
| 6,663,605 B2 | 12/2003 | Chan |
| 6,673,115 B2 | 1/2004 | Resch et al. |
| 6,702,817 B2 | 3/2004 | Beger et al. |
| 6,712,822 B2 | 3/2004 | Re et al. |
| 6,755,815 B2 | 6/2004 | Schultz |
| 6,755,836 B1 | 6/2004 | Lewis |
| 6,780,188 B2 | 8/2004 | Clark et al. |
| 6,827,722 B1 * | 12/2004 | Schoenefeld ...... A61B 17/1622 |
| | | 606/104 |
| 6,871,740 B1 | 3/2005 | Cao |
| 6,875,214 B2 | 4/2005 | Supinski |
| 6,875,216 B2 | 4/2005 | Wolf |
| 6,887,271 B2 | 5/2005 | Justin et al. |
| 6,939,379 B2 | 9/2005 | Sklar |
| 6,942,664 B1 | 9/2005 | Voor et al. |
| 6,955,678 B2 | 10/2005 | Gabriel et al. |
| 7,074,203 B1 * | 7/2006 | Johanson ............... A61F 2/0805 |
| | | 411/34 |
| 7,083,647 B1 | 8/2006 | Sklar et al. |
| 7,104,999 B2 | 9/2006 | Overaker |
| 7,204,839 B2 | 4/2007 | Dreyfuss et al. |
| 7,235,060 B2 | 6/2007 | Kraus |
| 7,261,716 B2 | 8/2007 | Strobel et al. |

(56) References Cited

U.S. PATENT DOCUMENTS

| | | | |
|---|---|---|---|
| 7,309,346 B2 | 12/2007 | Martinek | |
| 7,309,355 B2 | 12/2007 | Donnelly et al. | |
| 7,329,272 B2 * | 2/2008 | Burkhart | A61B 17/0401 |
| | | | 606/148 |
| 7,341,591 B2 | 3/2008 | Grinberg | |
| 7,341,592 B1 | 3/2008 | Walters et al. | |
| 7,413,542 B2 | 8/2008 | Kucklick et al. | |
| 7,442,202 B2 | 10/2008 | Dreyfuss | |
| 7,468,074 B2 | 12/2008 | Caborn et al. | |
| 7,476,228 B2 | 1/2009 | Abdou | |
| 7,481,830 B2 | 1/2009 | Wall et al. | |
| 7,556,638 B2 | 7/2009 | Morgan et al. | |
| 7,572,283 B1 | 8/2009 | Meridew | |
| 7,588,575 B2 | 9/2009 | Colleran et al. | |
| 7,611,521 B2 | 11/2009 | Lubbers et al. | |
| 7,651,528 B2 | 1/2010 | Montgomery et al. | |
| 7,697,861 B2 | 4/2010 | Shindo et al. | |
| D615,572 S | 5/2010 | Harpaz | |
| 7,713,300 B2 | 5/2010 | Meridew et al. | |
| 7,736,364 B2 | 6/2010 | Stone | |
| 7,766,920 B2 * | 8/2010 | Ciccone | A61B 17/1615 |
| | | | 606/104 |
| 7,828,090 B2 | 11/2010 | Drivdahl et al. | |
| 7,833,244 B2 | 11/2010 | Cerundolo | |
| 7,837,731 B2 | 11/2010 | Sklar | |
| 7,883,510 B2 | 2/2011 | Kim et al. | |
| 7,909,826 B2 | 3/2011 | Serhan et al. | |
| 7,918,288 B2 | 4/2011 | Drivdahl et al. | |
| 7,922,730 B2 | 4/2011 | Raines, Jr. | |
| 7,959,650 B2 | 6/2011 | Kaiser et al. | |
| 7,963,952 B2 | 6/2011 | Wright, Jr. et al. | |
| 7,963,983 B2 | 6/2011 | Cerundolo | |
| 7,967,861 B2 | 6/2011 | Montgomery et al. | |
| 7,993,369 B2 * | 8/2011 | Dreyfuss | A61B 17/0401 |
| | | | 606/232 |
| 8,012,083 B2 | 9/2011 | Kucklick et al. | |
| 8,021,403 B2 | 9/2011 | Wall et al. | |
| 8,034,083 B2 | 10/2011 | Abdelgany et al. | |
| 8,043,308 B2 | 10/2011 | Bittenson | |
| 8,048,158 B2 | 11/2011 | Hays et al. | |
| 8,051,929 B2 | 11/2011 | Drivdahl et al. | |
| 8,057,524 B2 | 11/2011 | Meridew | |
| 8,075,575 B2 | 12/2011 | Gonzalez-Hernandez | |
| 8,100,916 B2 * | 1/2012 | Kumar | A61B 17/7082 |
| | | | 606/104 |
| 8,123,749 B2 | 2/2012 | Serhan et al. | |
| 8,128,658 B2 | 3/2012 | Kaiser et al. | |
| 8,187,309 B2 | 5/2012 | Castaneda et al. | |
| 8,202,295 B2 | 6/2012 | Kaplan | |
| 8,206,446 B1 | 6/2012 | Montgomery | |
| 8,216,131 B2 | 7/2012 | Kucklick | |
| 8,221,455 B2 | 7/2012 | Shurnas et al. | |
| 8,221,498 B2 | 7/2012 | Boucher et al. | |
| 8,226,714 B2 | 7/2012 | Beck, Jr. et al. | |
| 8,231,654 B2 | 7/2012 | Kaiser et al. | |
| 8,241,298 B2 | 8/2012 | Sengun et al. | |
| 8,273,086 B2 | 9/2012 | Serhan et al. | |
| 8,277,464 B2 | 10/2012 | Bittenson | |
| 8,282,651 B2 | 10/2012 | Ciccone et al. | |
| 8,292,555 B2 | 10/2012 | Shaffer | |
| 8,328,716 B2 | 12/2012 | Schmieding et al. | |
| 8,343,195 B2 | 1/2013 | Rathbun et al. | |
| 8,348,972 B2 | 1/2013 | Soltz et al. | |
| 8,361,152 B2 | 1/2013 | McCormack et al. | |
| 8,377,089 B2 | 2/2013 | Lipchitz et al. | |
| 8,430,909 B2 | 4/2013 | Dreyfuss | |
| 8,435,293 B2 | 5/2013 | Donnelly et al. | |
| 8,435,294 B2 | 5/2013 | Montgomery et al. | |
| 8,465,545 B2 | 6/2013 | Montgomery et al. | |
| 8,506,573 B2 | 8/2013 | Dreyfuss et al. | |
| 8,512,376 B2 | 8/2013 | Thornes | |
| 8,512,405 B2 | 8/2013 | Baird | |
| 8,523,902 B2 | 9/2013 | Heaven et al. | |
| 8,523,903 B2 | 9/2013 | Kilburn-Peterson et al. | |
| 8,529,610 B2 | 9/2013 | Graf et al. | |
| 8,535,377 B2 | 9/2013 | Myers et al. | |
| 8,545,535 B2 | 10/2013 | Hirotsuka et al. | |
| 8,562,680 B2 | 10/2013 | Hays et al. | |
| 8,608,765 B1 | 12/2013 | Jurbala | |
| 8,617,197 B2 | 12/2013 | Friedman et al. | |
| 8,617,219 B2 | 12/2013 | Oren et al. | |
| 8,636,799 B2 | 1/2014 | Sklar et al. | |
| 8,647,385 B2 | 2/2014 | Boucher et al. | |
| 8,663,279 B2 | 3/2014 | Burkhart et al. | |
| 8,663,325 B2 * | 3/2014 | Graf | A61B 17/0401 |
| | | | 606/300 |
| 8,672,960 B2 | 3/2014 | Briganti et al. | |
| 8,672,967 B2 | 3/2014 | DiMatteo et al. | |
| 8,672,968 B2 | 3/2014 | Stone et al. | |
| 8,721,650 B2 | 5/2014 | Fanton et al. | |
| 8,747,470 B2 | 6/2014 | Beck, Jr. et al. | |
| 8,758,227 B2 | 6/2014 | Kucklick et al. | |
| 8,771,223 B2 | 7/2014 | Patton et al. | |
| 8,771,303 B1 | 7/2014 | Jurbala | |
| 8,778,023 B2 | 7/2014 | Sklar | |
| 8,784,431 B1 | 7/2014 | Harder et al. | |
| 8,790,368 B2 | 7/2014 | Sullivan et al. | |
| 8,821,383 B2 * | 9/2014 | Mirza | A61B 1/00135 |
| | | | 600/114 |
| 8,821,527 B2 | 9/2014 | Farnan et al. | |
| 8,821,557 B2 * | 9/2014 | Corradi | A61B 17/064 |
| | | | 606/308 |
| 8,840,665 B2 | 9/2014 | Young et al. | |
| 8,845,725 B2 | 9/2014 | Barwood et al. | |
| 8,870,877 B2 | 10/2014 | Koogle, Jr. | |
| 8,932,354 B2 | 1/2015 | Barwood et al. | |
| 8,939,983 B2 | 1/2015 | Stone et al. | |
| 8,956,410 B2 | 2/2015 | Donnelly et al. | |
| 9,056,010 B2 | 6/2015 | Shea et al. | |
| 9,060,748 B2 | 6/2015 | Housman et al. | |
| 9,060,772 B2 | 6/2015 | Gonzalez-Hernandez | |
| 9,095,331 B2 | 8/2015 | Hernandez et al. | |
| 9,241,783 B2 * | 1/2016 | Trenhaile | A61F 2/0805 |
| 9,277,911 B2 | 3/2016 | Hernandez | |
| 9,289,283 B2 | 3/2016 | Baird | |
| 9,301,751 B2 | 4/2016 | Sullivan et al. | |
| 9,314,240 B2 * | 4/2016 | Paulk | A61F 2/0811 |
| 9,693,856 B2 * | 7/2017 | Sengun | A61F 2/0805 |
| 9,795,412 B2 * | 10/2017 | Sinha | A61B 17/68 |
| 9,833,229 B2 | 12/2017 | Hernandez et al. | |
| 10,231,823 B2 | 3/2019 | Piccirillo et al. | |
| 10,231,824 B2 | 3/2019 | Piccirillo et al. | |
| 2001/0021855 A1 * | 9/2001 | Levinson | A61B 17/0057 |
| | | | 606/144 |
| 2002/0077631 A1 | 6/2002 | Lubbers et al. | |
| 2002/0151977 A1 | 10/2002 | Paes et al. | |
| 2002/0164218 A1 | 11/2002 | Aguirre | |
| 2002/0188301 A1 | 12/2002 | Dallara et al. | |
| 2003/0125749 A1 | 7/2003 | Yuan et al. | |
| 2003/0153921 A1 | 8/2003 | Stewart et al. | |
| 2003/0153926 A1 | 8/2003 | Schmieding et al. | |
| 2003/0225456 A1 * | 12/2003 | Ek | A61B 17/1675 |
| | | | 623/20.14 |
| 2003/0233095 A1 | 12/2003 | Urbanski et al. | |
| 2004/0068262 A1 * | 4/2004 | Lemos | A61F 2/0811 |
| | | | 424/426 |
| 2004/0073219 A1 | 4/2004 | Skiba et al. | |
| 2004/0073222 A1 | 4/2004 | Koseki | |
| 2004/0176767 A1 | 9/2004 | Bickley | |
| 2004/0193217 A1 * | 9/2004 | Lubbers | A61B 17/0401 |
| | | | 606/232 |
| 2004/0230194 A1 | 11/2004 | Urbanski et al. | |
| 2004/0267361 A1 | 12/2004 | Donnelly et al. | |
| 2005/0075668 A1 | 4/2005 | Lizardi | |
| 2005/0251137 A1 | 11/2005 | Ball | |
| 2006/0004378 A1 | 1/2006 | Raines et al. | |
| 2006/0015110 A1 | 1/2006 | Pepper | |
| 2006/0116685 A1 | 6/2006 | Urbanski et al. | |
| 2007/0005068 A1 | 1/2007 | Sklar | |
| 2007/0156153 A1 | 7/2007 | Jiang et al. | |
| 2007/0162124 A1 | 7/2007 | Whittaker | |
| 2007/0255172 A1 | 11/2007 | Pflueger | |
| 2007/0288031 A1 | 12/2007 | Dreyfuss et al. | |
| 2008/0027430 A1 | 1/2008 | Montgomery et al. | |

(56) References Cited

U.S. PATENT DOCUMENTS

| | | |
|---|---|---|
| 2008/0109038 A1 | 5/2008 | Steiner et al. |
| 2008/0161864 A1 | 7/2008 | Beck et al. |
| 2008/0215060 A1 | 9/2008 | Garcia et al. |
| 2008/0228186 A1 | 9/2008 | Gall et al. |
| 2008/0228224 A1 | 9/2008 | Sauer et al. |
| 2008/0275431 A1 | 11/2008 | Stone et al. |
| 2008/0275469 A1 | 11/2008 | Fanton et al. |
| 2009/0112270 A1 | 4/2009 | Lunn et al. |
| 2009/0138043 A1 | 5/2009 | Kohm |
| 2009/0171400 A1 | 7/2009 | van der Burg et al. |
| 2009/0192608 A1 | 7/2009 | Paulos |
| 2009/0275994 A1* | 11/2009 | Phan ............... A61B 17/7064 606/86 A |
| 2009/0281581 A1 | 11/2009 | Berg |
| 2009/0287259 A1 | 11/2009 | Trenhaile et al. |
| 2009/0312763 A1 | 12/2009 | McCormack et al. |
| 2009/0312782 A1 | 12/2009 | Park |
| 2009/0318923 A1 | 12/2009 | Burkhart et al. |
| 2010/0016869 A1 | 1/2010 | Paulk et al. |
| 2010/0069958 A1 | 3/2010 | Sullivan et al. |
| 2010/0106194 A1* | 4/2010 | Bonutti ............... A61B 17/17 606/279 |
| 2010/0121348 A1* | 5/2010 | van der Burg ..... A61B 17/0401 606/139 |
| 2010/0130989 A1 | 5/2010 | Bourque et al. |
| 2010/0145395 A1 | 6/2010 | Graf et al. |
| 2010/0174369 A1 | 7/2010 | Wang et al. |
| 2010/0198271 A1 | 8/2010 | Leone |
| 2010/0217393 A1 | 8/2010 | Theofilos |
| 2010/0241124 A1* | 9/2010 | Housman ........... A61B 17/0401 606/80 |
| 2010/0249801 A1 | 9/2010 | Sengun et al. |
| 2011/0004247 A1* | 1/2011 | Lechmann ........... A61B 17/7064 606/247 |
| 2011/0009885 A1 | 1/2011 | Graf et al. |
| 2011/0015675 A1 | 1/2011 | Howard et al. |
| 2011/0071579 A1 | 3/2011 | Reach, Jr. |
| 2011/0098727 A1 | 4/2011 | Kaiser et al. |
| 2011/0106013 A1 | 5/2011 | Whittaker et al. |
| 2011/0106252 A1* | 5/2011 | Barwood ............... A61F 2/0811 623/13.14 |
| 2011/0106253 A1* | 5/2011 | Barwood ............... A61F 2/0811 623/13.14 |
| 2011/0112550 A1 | 5/2011 | Heaven et al. |
| 2011/0112558 A1 | 5/2011 | Whayne et al. |
| 2011/0251621 A1 | 10/2011 | Sluss et al. |
| 2011/0257691 A1* | 10/2011 | Sutterlin ............... A61B 17/862 606/305 |
| 2011/0270323 A1* | 11/2011 | Olsen ............... A61B 17/862 606/305 |
| 2012/0010668 A1 | 1/2012 | Shimko |
| 2012/0057949 A1* | 3/2012 | Canizares, Jr. ....... A61B 17/862 411/410 |
| 2012/0059379 A1 | 3/2012 | Homan et al. |
| 2012/0109156 A1 | 5/2012 | Overes et al. |
| 2012/0109299 A1 | 5/2012 | Li et al. |
| 2012/0116459 A1* | 5/2012 | Nottmeier ........... A61B 17/7064 606/279 |
| 2012/0130374 A1 | 5/2012 | Bouduban et al. |
| 2012/0136357 A1 | 5/2012 | Torrie et al. |
| 2012/0150190 A1 | 6/2012 | Rabiner et al. |
| 2012/0150301 A1 | 6/2012 | Gamache et al. |
| 2012/0211543 A1 | 8/2012 | Euteneuer |
| 2012/0215232 A1* | 8/2012 | Olsen ............... A61B 17/1728 606/139 |
| 2012/0245686 A1 | 9/2012 | Park |
| 2012/0316565 A1* | 12/2012 | Stark ............... A61B 17/025 606/80 |
| 2013/0006302 A1* | 1/2013 | Paulk ............... A61B 17/0401 606/232 |
| 2013/0103054 A1 | 4/2013 | Housman |
| 2013/0103080 A1 | 4/2013 | Hernandez |
| 2013/0125714 A1* | 5/2013 | Dahners ............ A61B 17/8615 81/451 |
| 2013/0158597 A1 | 6/2013 | Hernandez |
| 2013/0158664 A1 | 6/2013 | Palmatier et al. |
| 2013/0190817 A1* | 7/2013 | Bouduban ............ A61B 17/0401 606/232 |
| 2013/0197534 A1 | 8/2013 | Lauderbaugh et al. |
| 2013/0197591 A1* | 8/2013 | Corradi ............... A61B 17/064 606/308 |
| 2013/0238036 A1* | 9/2013 | Sinha ............... A61B 17/68 606/304 |
| 2013/0267998 A1 | 10/2013 | Vijay et al. |
| 2013/0268010 A1* | 10/2013 | Santangelo ........ A61B 17/8883 606/304 |
| 2013/0310842 A1 | 11/2013 | Winkler et al. |
| 2013/0325128 A1 | 12/2013 | Perloff et al. |
| 2013/0331942 A1 | 12/2013 | Baird |
| 2013/0338710 A1 | 12/2013 | Heaven et al. |
| 2014/0005686 A1 | 1/2014 | Patton et al. |
| 2014/0046369 A1 | 2/2014 | Heaven et al. |
| 2014/0081324 A1 | 3/2014 | Sengun |
| 2014/0107713 A1 | 4/2014 | Pech et al. |
| 2014/0171983 A1 | 6/2014 | Graf et al. |
| 2014/0172095 A1 | 6/2014 | Graf et al. |
| 2014/0188166 A1 | 7/2014 | Cobb et al. |
| 2014/0228898 A1 | 8/2014 | Gordon |
| 2014/0236183 A1 | 8/2014 | Graf et al. |
| 2014/0243978 A1 | 8/2014 | Beck, Jr. et al. |
| 2014/0243982 A1 | 8/2014 | Miller |
| 2014/0249579 A1 | 9/2014 | Heaven et al. |
| 2014/0257384 A1 | 9/2014 | Dreyfuss et al. |
| 2014/0277133 A1 | 9/2014 | Foerster |
| 2014/0277134 A1 | 9/2014 | ElAttrache et al. |
| 2014/0309668 A1 | 10/2014 | Sullivan et al. |
| 2014/0343604 A1 | 11/2014 | Frank |
| 2014/0364862 A1 | 12/2014 | Bennett et al. |
| 2015/0018878 A1 | 1/2015 | Rizk et al. |
| 2015/0018947 A1 | 1/2015 | Barwood |
| 2015/0039030 A1 | 2/2015 | Saliman et al. |
| 2015/0066042 A1 | 3/2015 | Cummins et al. |
| 2015/0173741 A1* | 6/2015 | Housman ........... A61B 17/0401 606/232 |
| 2015/0190130 A1 | 7/2015 | Groh |
| 2015/0238327 A1 | 8/2015 | Cheng et al. |
| 2016/0113643 A1* | 4/2016 | Diduch et al. ..... A61B 17/0401 606/232 |
| 2016/0113644 A1* | 4/2016 | Diduch ............... A61F 2/0811 606/104 |
| 2016/0113756 A1* | 4/2016 | Diduch ............... A61F 2/0811 623/13.14 |
| 2016/0113757 A1* | 4/2016 | Diduch ............... A61F 2/0805 606/104 |
| 2016/0113758 A1* | 4/2016 | Diduch ............... A61F 2/0811 606/232 |
| 2016/0310260 A1 | 10/2016 | Sengun et al. |
| 2017/0265988 A1 | 9/2017 | Sengun et al. |
| 2017/0290655 A1 | 10/2017 | Piccirillo et al. |
| 2017/0290656 A1 | 10/2017 | Piccirillo et al. |
| 2018/0296319 A1 | 10/2018 | Diduch et al. |
| 2018/0344376 A1* | 12/2018 | Diduch ............... A61B 17/88 |
| 2019/0029805 A1 | 1/2019 | Piccirillo et al. |
| 2019/0029806 A1 | 1/2019 | Piccirillo et al. |
| 2020/0008928 A1 | 1/2020 | Diduch et al. |
| 2020/0129171 A1 | 4/2020 | Diduch et al. |

FOREIGN PATENT DOCUMENTS

| | | |
|---|---|---|
| CN | 101394795 A | 3/2009 |
| CN | 102098969 A | 6/2011 |
| CN | 102292032 A | 12/2011 |
| CN | 102438548 A | 5/2012 |
| CN | 102470007 A | 5/2012 |
| CN | 202515702 U | 11/2012 |
| CN | 102905629 A | 1/2013 |
| CN | 103209647 A | 7/2013 |
| CN | 103445850 A | 12/2013 |
| CN | 203789970 | 8/2014 |
| DE | 10325139 A1 | 12/2004 |
| EP | 1110510 A1 | 6/2001 |
| EP | 1 491 162 A2 | 12/2004 |

(56) References Cited

FOREIGN PATENT DOCUMENTS

| | | |
|---|---|---|
| EP | 2 327 374 A1 | 6/2011 |
| EP | 2918238 A1 | 9/2015 |
| EP | 3020371 A2 | 5/2016 |
| EP | 2918238 B1 | 11/2017 |
| JP | 200513740 A | 1/2005 |
| JP | 2005-66135 A | 3/2005 |
| JP | 2005-506864 A | 3/2005 |
| JP | 2005-323700 A | 11/2005 |
| JP | 2007-50269 A | 3/2007 |
| JP | 2007-306979 A | 11/2007 |
| JP | 200886769 A | 4/2008 |
| JP | 2011516795 A | 5/2011 |
| JP | 2011-528270 A | 11/2011 |
| JP | 2014-171673 A | 9/2014 |
| WO | WO-9428799 A1 | 12/1994 |
| WO | 97/31517 A2 | 8/1997 |
| WO | WO-0130253 A1 | 5/2001 |
| WO | WO-2007110863 A2 | 10/2007 |
| WO | 2009/055800 A1 | 4/2009 |
| WO | 2012129206 A2 | 9/2012 |
| WO | WO-2012125905 A1 | 9/2012 |
| WO | WO-2012129617 A1 | 10/2012 |
| WO | WO-2012138777 A1 | 10/2012 |
| WO | WO-2014150053 A1 | 9/2014 |

OTHER PUBLICATIONS

European Search Report for EP Application No. 15191002.3, dated Apr. 15, 2016. (8 pages).
European Search Report for EP Application No. 15191010.6, dated Apr. 4, 2016. (6 pages).
European Search Report for EP Application No. 15191011.4, dated Apr. 1, 2016. (6 pages).
European Search Report for EP Application No. 15191013.0, dated Apr. 14, 2016. (7 pages).
European Search Report for EP Application No. 16166686.2, dated Sep. 20, 2016. (8 pages).
European Search Report for EP Application No. 17165700.0, dated Aug. 11, 2017. (12 pages).
European Search Report for EP Application No. 17165749.7, dated Aug. 21, 2017.
Chinese Search Report issued in related CN Application No. 201510696822.2 (5 pages).
Translation of International Search Report for CN Application No. 201510697570.5 dated Mar. 1, 2019 (3 pages).
Translation of Chinese Search Report for CN Application No. 201510696510.1 dated May 26, 2019 (4 pages).
Chinese Search Report for CN Application No. 201510696528.1 dated Jun. 25, 2019 (16 pages).

* cited by examiner

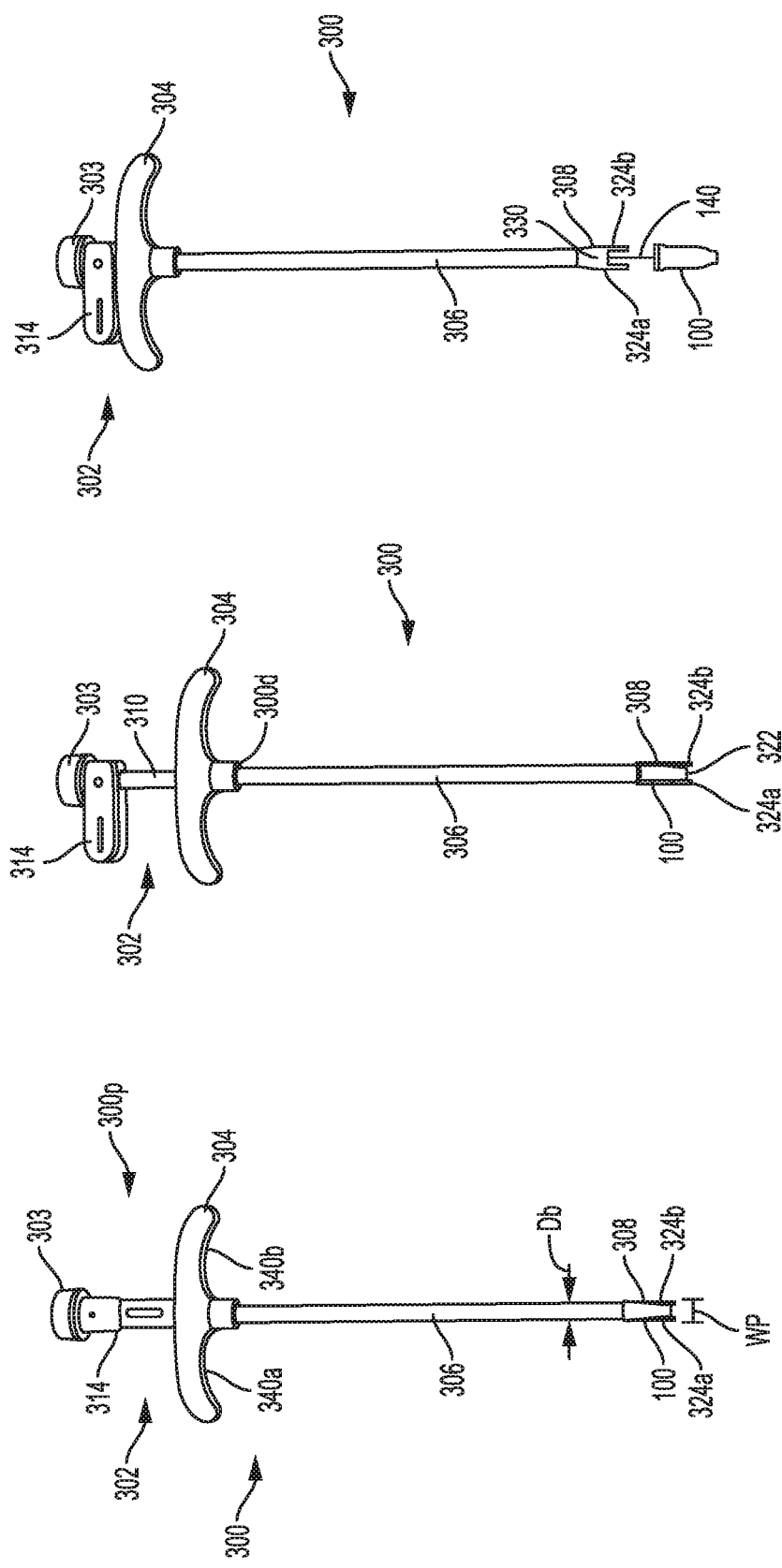

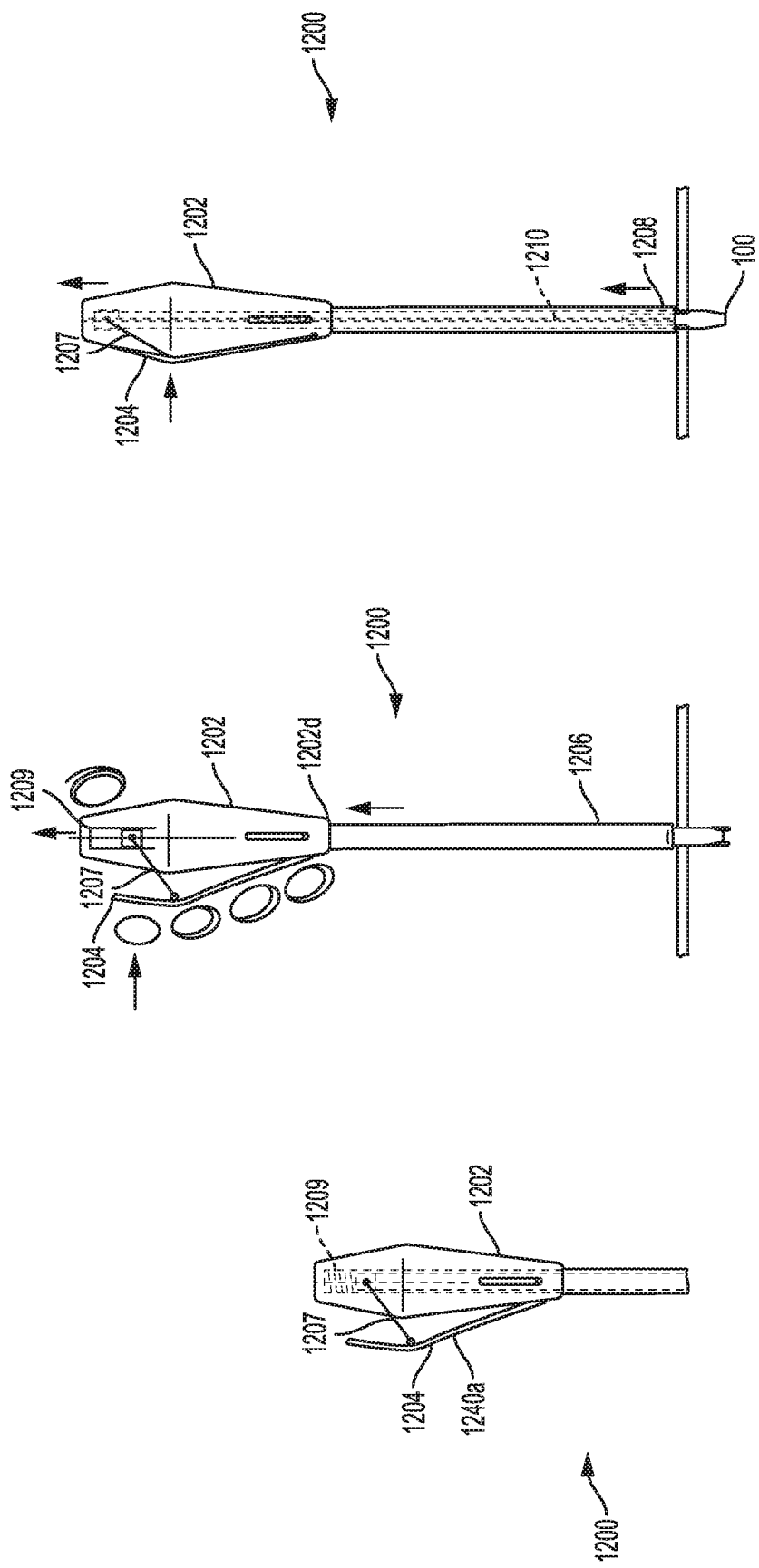

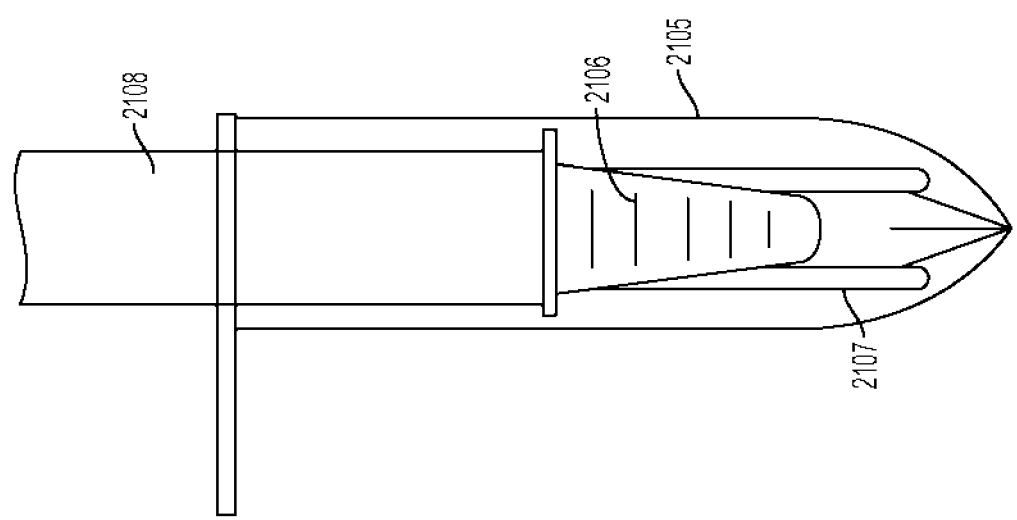

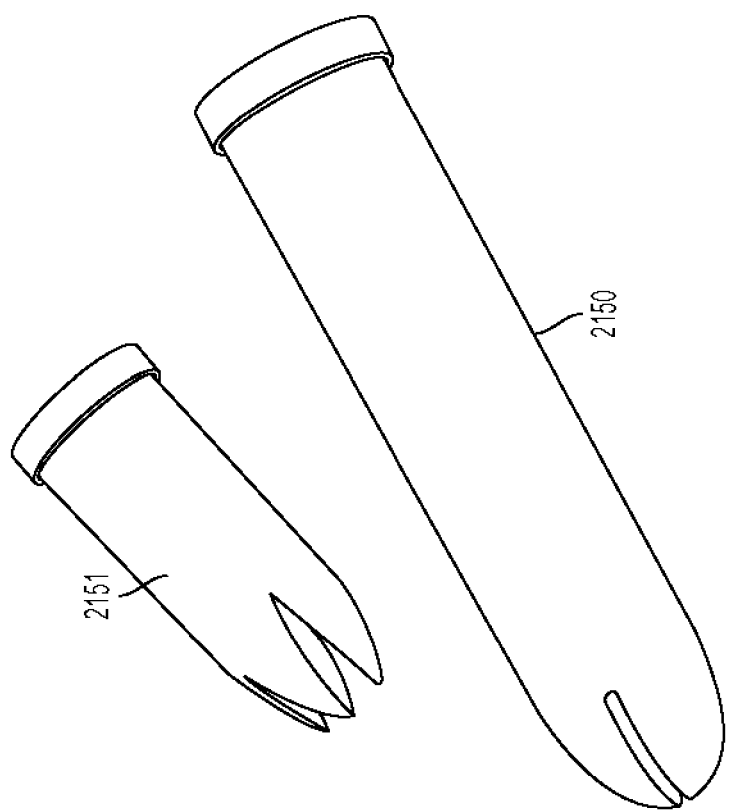

BICEPS TENODESIS DELIVERY TOOLS

CROSS-REFERENCE TO RELATED APPLICATIONS

The present application is a divisional of U.S. patent application Ser. No. 14/610,730 filed Jan. 30, 2015, entitled "BICEPS TENODESIS DELIVERY TOOLS," which claims priority to U.S. Provisional Appl. No. 62/067,701 filed on Oct. 23, 2014 and entitled "Biceps Tenodesis Implants and Delivery Devices," which are hereby incorporated by reference in their entireties.

FIELD

Surgical devices and methods are provided for anchoring tissue to bone, and more particularly surgical implants, delivery tools, and methods are provided for securing a biceps tendon to the humerus.

BACKGROUND

Disorders of the long head of the biceps tendon are a common source of shoulder pain and may occur in association with other diagnoses such as rotator cuff tears, superior labrum anterior posterior tears, impingement syndrome and capsular injuries, or may be present as an isolated source of shoulder pain. The treatment options for disorders of the long head of the biceps (LHB) continue to evolve and can include LHB tenodesis. In a tenodesis procedure, a suture is passed through the base of the LHB to locate the LHB in the subacromial space and to provide proximal control during the dissection. Once the suture is placed, the LHB is cut near the glenoid attachment. A sizer can be used to measure the tendon size and to thereby determine the appropriately sized bone screw. Once the screw is selected, a bone hole is drilled and a tendon fork is then used to push the tendon down into the bone hole. A bone screw is then delivered into the bone hole to anchor the tendon within the bone hole.

While current procedures can provide an effective means for anchoring a tendon to bone, they can suffer from several drawbacks. For example, current procedures require the use of numerous tools, which can lead to a prolonged procedure and increased costs. The use of a screw can also increase the risk of damage to the tendon, as rotation of the screw into the bone hole can tear through the tendon. Moreover, it can be difficult to maintain the desired tension on the tendon while the screw is being implanted, as the tendon can slip during insertion of the screw. Any tension applied to the tendon during insertion of the anchor can also cause the anchor to back-out of the bone hole.

Accordingly, there remains a need for improved methods and devices for anchoring tissue to bone, and in particular for performing a biceps tenodesis.

SUMMARY

Various implants, tools and methods are provided for attaching a biceps tendon to a bone.

In one embodiment, an anchor inserter tool is provided including a first elongate body having first and second prongs extending distally from a distal end thereof and configured to extend along opposed slots formed in a sheath of an anchor assembly. The anchor inserter tool can additionally include a second elongate body slidably disposed relative to the first elongate body, and a handle assembly coupled to a proximal end of the first and second elongate bodies. The handle assembly can include a locking mechanism that is movable between a locked position, in which the locking mechanism prevents movement of the first and second elongate bodies relative to one another, and an unlocked position in which the first and second elongate bodies are axially slidable relative to one another.

In various embodiments, the first elongate body of the anchor inserter tool can be an inner shaft and the second elongate body can be an outer shaft disposed around the inner shaft. In other embodiments, the second elongate body of the anchor inserter tool can be an inner shaft and the first elongate body can be an outer shaft disposed around the inner shaft. In other aspects, the first elongate body can include a lumen configured to receive a proximal end of a guidewire coupled to a sheath of an anchor assembly. The handle assembly can include a guidewire lock configured to selectively engage and prevent movement of a guidewire disposed within the handle.

In other embodiments, the handle assembly can include an actuator coupled to the first elongate body and configured to move the first elongate body axially with respect to the second elongate body. The actuator can be rotatable relative to the handle assembly such that rotation of the actuator is effective to cause axial translation of the inner and outer shafts relative to one another. In other aspects, the actuator can be pivotable relative to the handle assembly such that pivotal movement of the actuator is effective to cause axial translation of the inner and outer shafts relative to one another.

Some embodiments can include an actuator with at least one handle extending in a perpendicular direction from the first elongate body. In other embodiments the actuator can extend proximally from the proximal end of the first elongate body. The actuator can include at least one finger loop.

In another embodiment, the handle assembly can have a pistol-grip configuration with a stationary housing and a pivotable trigger. The first elongate body can be an inner shaft and the second elongate body can be an outer shaft disposed around the inner shaft, and the handle assembly can include an actuator configured to move the inner shaft proximally with respect to the outer shaft to retract the first and second prongs of the inner shaft into the outer shaft.

In another embodiment, a tendon anchoring system is provided with an outer shaft having an inner lumen extending therethrough and a sheath alignment protrusion formed on a distal end thereof. The tendon anchoring system also includes an inner shaft disposed within the outer shaft and having first and second prongs formed on a distal end thereof, the prongs being movable between an extended position in which the prongs extend distally beyond the distal end of the outer shaft, and a retracted position in which the prongs are retracted into the distal end of the outer shaft. The prongs can extend along opposed sides of the sheath alignment protrusion on the outer shaft. The tendon anchoring system can further be provided with a handle assembly coupled to a proximal end of each of the first and second shafts.

In one embodiment, the sheath alignment feature can have a generally conical shape. In other aspects, the sheath alignment feature can include first and second opposed cut-outs formed therein and configured to receive the first and second prongs of the inner shaft. In another embodiment, the distal end of the outer shaft can be closed with an elongate slot formed therein for receiving the first and second prongs therethrough.

In other embodiments, a method for anchoring a tendon to bone is provided and includes manipulating an inserter tool to insert a sheath coupled to a distal end of the inserter tool through tissue, the sheath having a guidewire mated thereto and extending through the inserter tool. The method can additionally include positioning a tendon between a pair of prongs on a distal end of the inserter tool, and manipulating the inserter tool to advance the sheath, with the tendon between the prongs, into a bone hole. A locking mechanism on a handle assembly of the inserter tool can maintain the guidewire and the prongs in a locked position relative to one another. The method further can include moving the locking mechanism on the handle assembly to an unlocked position and manipulating the handle assembly to retract the prongs relative to the guidewire, and removing the inserter tool such that the sheath with the guidewire mated thereto remains in the bone hole.

The inserter tool can include first and second shafts. The prongs can be formed on the first shaft, and manipulating the handle assembly to retract the prongs relative to the guidewire can include moving the first shaft relative to the second shaft.

In various embodiments, the locking mechanism can extend between a handle on the first shaft and a handle on the second shaft to block movement of the first and second shafts relative to one another when the locking mechanism is in a locked position.

In another embodiment, the first shaft can include an actuator coupled to a proximal end thereof, and the locking mechanism can prevent movement of the actuator when in a locked position, and the locking mechanism can release the actuator when it is moved to the unlocked position. The locking mechanism can also extend through a handle of the inserter tool to block movement of the first and second shafts relative to one another when the locking mechanism is in a locked position. The locking mechanism can further include two separate elements, each operatable independently from one another to block movement of the first and second shafts relative to one another and separately to block movement of the guidewire.

BRIEF DESCRIPTION OF THE DRAWINGS

The invention will be more fully understood from the following detailed description taken in conjunction with the accompanying drawings, throughout which arrows can be used to represent possible motion, in which:

FIG. 1A is a side view of a sheath inserter tool and a sheath, showing a lock in a locked position;

FIG. 1B is another side view of the sheath inserter tool of FIG. 1A showing a lock in an unlocked position;

FIG. 1C is another side view of the sheath inserter tool of FIG. 1B with an actuator moved proximally;

FIG. 11A is a side view of a handle portion of yet another embodiment of a sheath inserter tool;

FIG. 11B is a side view of the sheath inserter tool of FIG. 11A, showing a sheath mating thereto and being implanted in bone;

FIG. 11C is a side view of the sheath inserter tool of FIG. 11B, showing an inner shaft retracted from the sheath;

FIG. 23 is a side view of one embodiment of a sheath protector;

FIG. 28 is a side view of additional embodiments of a sheath protector;

DETAILED DESCRIPTION

Figure 2B:
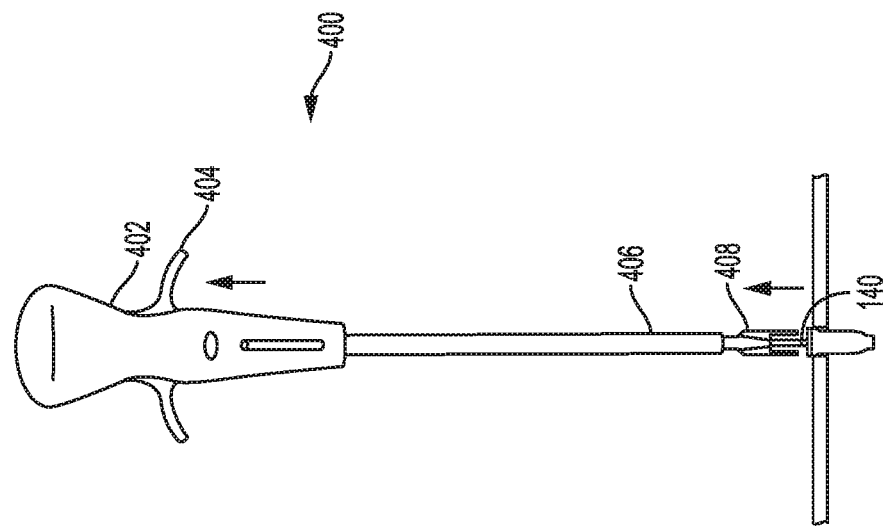
FIG. 2B a side view of the sheath inserter tool of FIG. 2A, showing an outer shaft retracted from the sheath.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

In general, methods and devices are provided for anchoring a ligament or tendon to bone. In an exemplary embodiment, the methods and devices are used to perform a biceps tenodesis, however a person skilled in the art will appreciate that the devices and methods can be used in various procedures and for anchoring any tissue to bone. In particular, various delivery tools for implanting a sheath of an anchor assembly within a bone hole are provided. The tools can be used to position a tendon within a prepared bone hole, and to deliver a sheath, and optionally a guidewire coupled to the sheath, into the bone hole. Once the sheath is implanted within a bone hole, a sheath expander can be inserted into the sheath, e.g., using a driver tool. The sheath expander will cause the sheath to expand, thereby anchoring the sheath, with the tendon positioned therearound, within the bone hole.

A person skilled in the art will appreciate that the delivery tools and methods disclosed herein can be used with a variety of implants and other surgical devices, including measuring devices, drills, and mallets, etc. In some embodiments, the system can include any one or more of the following components: an anchor assembly or an implant having a sheath and expander that is received within the sheath; a sheath inserter tool; a driver tool; and a loader. The components of the system can reduce the number of steps required to perform a biceps tenodesis, and can do so with minimal risk of injuring to the tendon. In an exemplary embodiment, the tools are configured for use with the anchors and drivers disclosed in U.S. patent application Ser. No. 14/610,618 entitled "Biceps Tenodesis Implants and Delivery Tools," and U.S. patent application Ser. No. 14/610,626 entitled "Biceps Tenodesis Anchor Implants," each of which is filed on even date herewith and incorporated by reference herein in its entirety.

The apparatus and methods described herein may have a number of advantages over existing techniques for preforming bicep tenodesis. In particular, the entire attachment preparation procedure can be straightforward and requires a surgeon to take only a few quick steps to affix the implant structure including the sheath and the expander to the bone. A risk of damaging the tendon during rotation of the expander or any other technique requiring rotation of a component in direct contact with the tendon may be avoided. As a result, a risk of causing trauma to the tendon can be reduced and the time required to prepare and affix the tendon can be significantly reduced, which can facilitate the surgery and mitigate inconvenience to the patient. In addition, the described techniques can help save operating room costs.

As indicated above, various inserter tools are provided for inserting a sheath into a bone hole. The inserter tools can also be used to perform various other functions in connection with insertion of the sheath into a bone hole. For example, the inserter tools can be effective to initially measure a size of a tendon. Multiple inserter tools having different sizes can be provided, with the sizes corresponding to the appropriately sized sheath to be used therewith. The inserter tools can also be configured to insert or "plunge" a tendon into a pre-drilled bone hole, and to maintain the tendon within the bone hole while delivering a sheath into the bone hole. The inserter tools can further be configured to receive a guidewire therein that is coupled to the sheath. This can allow the sheath with the guidewire mated thereto to be delivered into a bone hole, and the guidewire can thereafter remain with the sheath and facilitate delivery of the an expander into the sheath. In certain exemplary embodiments, the inserter tool can be configured to fixedly engage the guidewire to prevent movement thereof during plunging of the tendon and during delivery of the sheath, and it can be configured to selectively release the guidewire once the sheath is implanted to allow the tool to be removed from the guidewire, leaving the sheath implanted with the guidewire extending therefrom.

FIGS. 1A-1C illustrate one exemplary embodiment of a sheath inserter tool shown having a sheath coupled thereto. As shown, the sheath inserter tool 300 generally includes a handle assembly 302 having a proximal end 300p with a proximal knob 303 and a distal end 300d with a distal actuator 304. The actuator 304 is coupled to a proximal end of an outer shaft 306 that extends distally from the actuator 304. The knob 303 is coupled to a proximal end of an inner shaft 310 that is slidably coupled to and extends proximally from the actuator 304. While not shown, the inner shaft 310 can include a distal end that mates to the actuator 304 such that the actuator 304 and outer shaft 306 are slidably movable relative to the inner shaft 310, but that prevents disengagement of the inner shaft 310 from the actuator 304 and outer shaft 306. By way of non-limiting example, the mating feature can be in the form of a flange formed on a distal end of the inner shaft 310 and sized larger than an opening formed in a proximal end of the actuator 304 to prevent passage of the flange therethrough. The outer shaft 306 can also include features at a distal end thereof for interacting with a sheath, as will be discussed below. Moreover, the sheath inserter tool 300 can include a locking mechanism for controlling movement of the inner and outer shafts 310, 306 relative to one another, as will be discussed in more detail below.

The actuator 304 can have a variety of configurations, but in the illustrated embodiment, the actuator 304 on the outer component has a general T-shape configuration to facilitate grasping thereof. The actuator 304 can have a blind bore extending therein from the distal end 300d and terminating just distal to the proximal-most end. The blind bore can be configured to receive a proximal end of the outer shaft 306 for mating the shaft to the actuator 304. In an exemplary embodiment, the proximal end of the outer shaft 306 is fixedly and non-movably mated to the actuator 304, e.g., using adhesive, welding, a threaded engagement, or any other mating mechanism known in the art.

The actuator 304 can also include various features to facilitate grasping and actuation thereof. As shown, the actuator 304 extends laterally outward with respect to the shaft 306 and includes distal facing finger-gripping surfaces 340a, 340b. The proximal end 300p of the handle assembly 302 can be placed in a user's palm and the user's fingers can be positioned within the finger-gripping surfaces 340a, 340b to allow the user to pull the actuator 304 proximally with respect to the inner shaft 310 and knob 303. Since the actuator 304 is fixedly and non-movably mated to the outer shaft 306, movement of the actuator 304 relative to the knob 303 moves the outer shaft 306 relative to the inner shaft 310.

The knob 303 of the handle assembly 302 can also have a variety of configurations. In the illustrated embodiment, the knob 303 is generally cylindrical and is fixedly mated to a proximal end of the inner shaft 310. Various mating techniques, such as those described above, can be used to mate the two components.

As indicated above, the outer shaft 306 is coupled to and extends from the actuator 304 and can have a generally elongate cylindrical shape with a fork 308 on a distal end 300d thereof. The fork 308 can function to both measure a tendon, and to facilitate insertion of the tendon and sheath 100 into a bone hole. As shown, the fork 308 includes first and second elongate prongs 324a, 324b that are configured to extend longitudinally along opposed sides of the sheath 100 when the sheath is coupled to the distal end of the outer shaft 306. The elongate prongs 324a, 324b can each have various shapes, such as a square or rectangular cross-sectional shape. The fork prongs 324a, 324b preferably have a maximum width Wp that is sized to fit within a bone tunnel sized to receive the sheath. The outer shaft 306 can also have an outer diameter $D_b$ that matches the maximum width Wp of the prongs, or in other embodiments the outer diameter $D_b$ of the outer shaft 306 can be greater than the maximum width Wp of the prongs to allow the distal end of the outer shaft 306 to act as a hard stop to limit an insertion depth of the prongs into a bone hole. The pair of prongs 324a, 324b can extend distally beyond the distal end of the outer shaft 306 by a predetermined distance D to thereby define a u-shaped recess 322 between the pair of prongs 324a, 324b. The u-shaped recess 322 can be configured to receive the sheath 100 therein, with the prongs 324a, 324b extending along the opposed sidewall cut-outs in the sheath 100.

As indicated above, the handle can include additional features for controlling movement of the inner and outer shafts 310, 306 relative to one another. As shown in FIGS. 1A-1C, the handle assembly 302 includes a lock 314 disposed between the knob 303 and the actuator 304. The lock can be mounted on the inner shaft 310 and it can be configured to rotate about its fixed point at the proximal end of the inner shaft 310. When in a locked position as shown in FIG. 1A, the lock 314 extends along the entire length of the inner shaft 310 and extends between the knob 303 and the actuator 304, thereby preventing proximal movement of the actuator 304 and thus preventing the inner and outer shafts 310, 306 from moving longitudinally with respect to each other. In order to move the actuator 304 and the outer shaft 306 proximally relative to the inner shaft 310, the lock 314 can be rotated 90 degrees to a perpendicular position, as shown in FIG. 1B. Since the lock 314 is no longer blocking movement of the actuator 304, the actuator 304 can be moved proximal from the position shown in FIG. 1B to the position shown in FIG. 1C.

This movement of the actuator 304 and outer shaft 310 coupled thereto is effective to retract the prongs on the distal end of the outer shaft 310 with respect to the sheath 100. In particular, as shown in FIG. 1C, the sheath can include a guidewire 140 mated thereto. The guidewire 140 can extend from the sheath 100, proximally through the outer shaft 306, and through the inner shaft 310. The knob 303 can include an internal feature for engaging the guidewire, such as threads formed therein for threadably mating to threads formed on a proximal end of the guidewire, or a compressible material that engages the guidewire by press-fit or any other technique known in the art. With the guidewire being mated to the knob 303, the knob 303 will maintain the guidewire, and the sheath mated thereto, in a fixed position during proximal movement of the actuator 304 and outer shaft 306 relative to the knob 303 and inner shaft 310. A person skilled in the art will appreciate that the guidewire does not need to be engaged within the knob, and in other embodiments the guidewire could be slid into the cannulation in the knob without being held by any engagement feature.

In use, the lock 314 is preferably in the longitudinal position, as seen in FIG. 1A, during insertion of the tool and sheath through tissue, such that the lock 314 effectively blocks the actuator 304 and prevents any movement of the inner and outer shafts 310, 306 relative to one another. In this configuration, the sheath 100 is loaded onto the distal end of the inserter and the fork 308 is in a fully extended position, extending distally beyond the sheath 100. As seen in FIG. 1B, upon rotation of the lock 314 to the unlocked position, the actuator 304 may be moved proximally. Proximal movement of the actuator 304 will move the outer shaft 306 proximally, as shown in FIG. 1C. The fork 308, attached to the outer shaft 306, is thus moved proximally and withdrawn from the sheath 100. The tool 300 can be removed leaving the sheath 100, with the guidewire attached thereto, implanted in the bone hole. As described in the aforementioned applications, incorporated herein by reference, a driver tool can then be used to insert an expander, such as a screw, into the sheath to thereby anchor the sheath and a tendon positioned therearound, within the bone hole. In an exemplary embodiment, the expander is delivered over the guidewire and into the sheath.

A person skilled in the art will appreciate that the various features shown with respect to FIGS. 1A-1C can be used in combination with any of the other devices disclosed herein, and that the features of the other devices disclosed herein can similarly be used with respect to FIGS. 1A-1C. By way of non-limiting example, each of the tools disclosed herein can include a guidewire grasper that is configured to engage and releasably retain a guidewire in a fixed position with respect to the inner or outer components of the tool, i.e., the component that does not have the fork. Moreover, each of the tools disclosed herein can additionally or alternatively include a locking mechanism that is configured to lock the inner and outer components relative to one another, and the locking mechanism can have any of the various configurations disclosed herein. The tools can also include other features, such as those disclosed in the above-referenced patent applications.

Figure 2A:
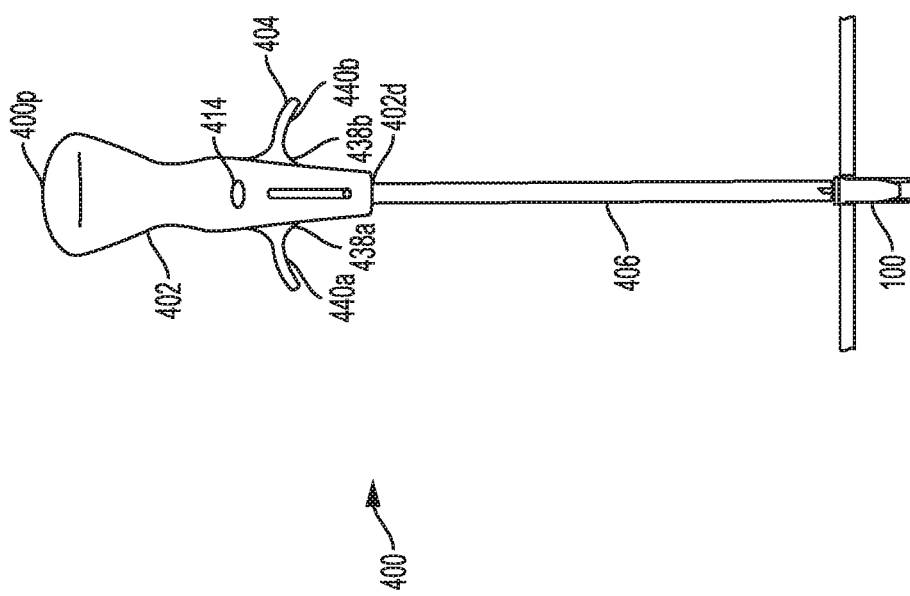
FIG. 2A is a side view of another embodiment of a sheath inserter tool, showing a sheath coupled to the device and being implanted in bone.

FIGS. 2A-B show another embodiment of a sheath inserter tool 400 that is similar to the embodiment of FIGS. 1A-1B, but that includes a different handle assembly. In particular, the tool 400 includes a handle 402 that is configured to releasably engage a guidewire 140 coupled to a sheath 100. An outer shaft 406 slides within and extends distally from the handle 402. A proximal end of the outer shaft 406 is disposed within the handle 402 and is coupled to an actuator 404. Both the actuator 404 and the outer shaft 406 are slidably movable with respect to the handle 402 to thereby allow the outer shaft 406, with the fork on the distal end thereof, to be retracted relative to the sheath and guidewire. The fork on the distal end of the inserter tool is not described in detail, as it can have the same configuration as the fork described above with respect to FIGS. 1A-1C.

The handle 402 in this embodiment has a generally elongate cylindrical configuration to facilitate grasping thereof. The handle 402 can have a blind bore extending therein from the distal end 402d and terminating just distal to the proximal-most end 400p. The bore can include a guidewire grasping element (not shown) for releasably engaging a guidewire. The grasping element can have a configuration as previously described with respect to FIGS. 1A-1C, or it can have a configuration as described in the aforementioned patent applications which are incorporated herein by reference. A distal portion of the bore can slidably receive the proximal end of the outer shaft 406. The handle 402 can further include elongate longitudinal cut-outs 438a, 438b formed in opposite sidewalls thereof and in communication with the bore. The cut-outs 438a, 438b can allow the actuator 404 to extend therethrough and to slidably move there along.

The actuator 404 in this embodiment is similar to the actuator of FIGS. 1A-1C and is generally T-shaped with distal facing finger-gripping surfaces 440a, 440b. The actuator 404 extends laterally outward from opposed sides of the handle 402, and thus allows a user to place the proximal end 400p of the handle 402 in their palm and to grasp the actuator 404 with one or more fingers to pull the actuator 404 proximally. The actuator can thus slide proximally and distally relative to the handle. The actuator 404 can be fixedly mated to or integrally formed on the proximal end of the outer shaft 406. As a result, movement of the actuator 404 relative to the handle 402 moves the outer shaft 406 relative to the handle 402 (once the lock 414 is released). While not shown, a person skilled in the art will appreciate that the guidewire extends through a lumen in the outer shaft, through a lumen in the actuator, and through the bore in the handle.

As indicated above, the handle can include additional features for controlling movement of the outer shaft 406 relative to the handle 402. As shown in FIGS. 2A-2B, the handle 402 includes a lock 414 disposed thereon. The lock 414 can be actuated by pressing the lock 414 into the handle 402. When in a locked position as shown in FIG. 2A, the lock 414 blocks proximal movement of the actuator 404 and thus locks the outer shaft 406 in a fixed position relative to the handle 402. In order to move the actuator 404 and the outer shaft 406 proximally relative to the handle 402 (thereby retracting the fork 408 relative to the guidewire and the sheath 100), the lock 414 must be moved to an unlocked position, shown in FIG. 2B, in which the actuator 404 is free to move proximally. Movement of the lock between the locked and unlocked positions can be achieved using, for example, a push-button mechanism having a rotating component that alternates between two positions, the locked and unlocked position.

Figure 3A:
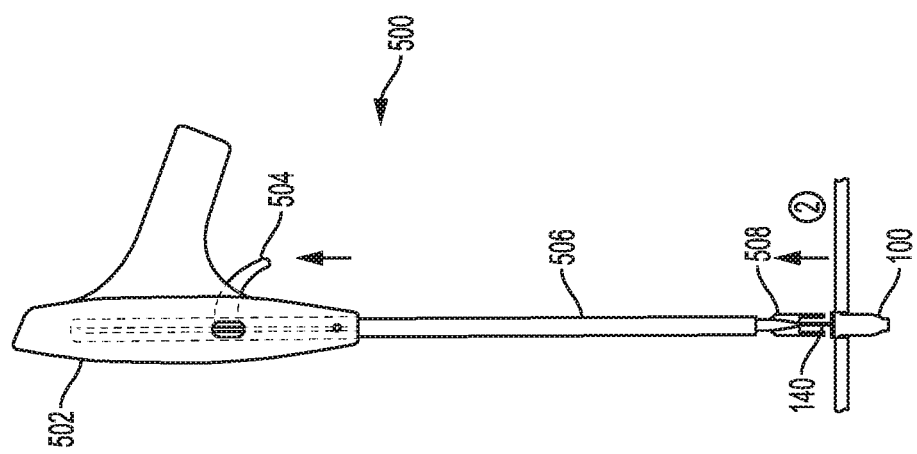
FIG. 3A is a side view of another embodiment of a sheath inserter tool.
Figure 3B:
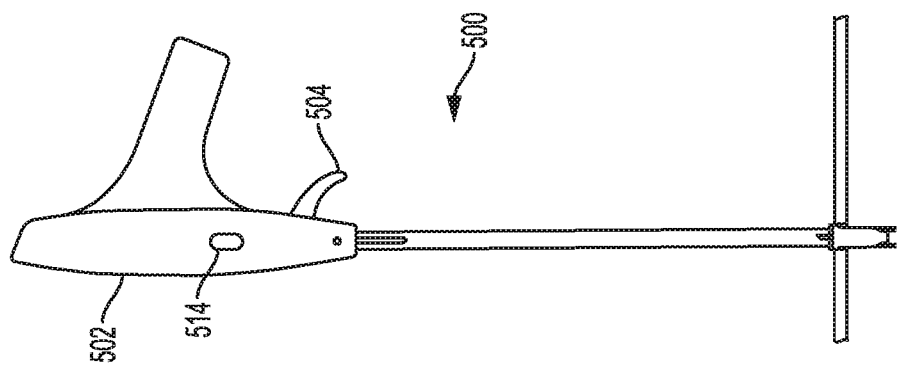
FIG. 3B is a side view of the sheath inserter tool of FIG. 3A, showing a sheath coupled to the device and being implanted in bone.
Figure 3C:
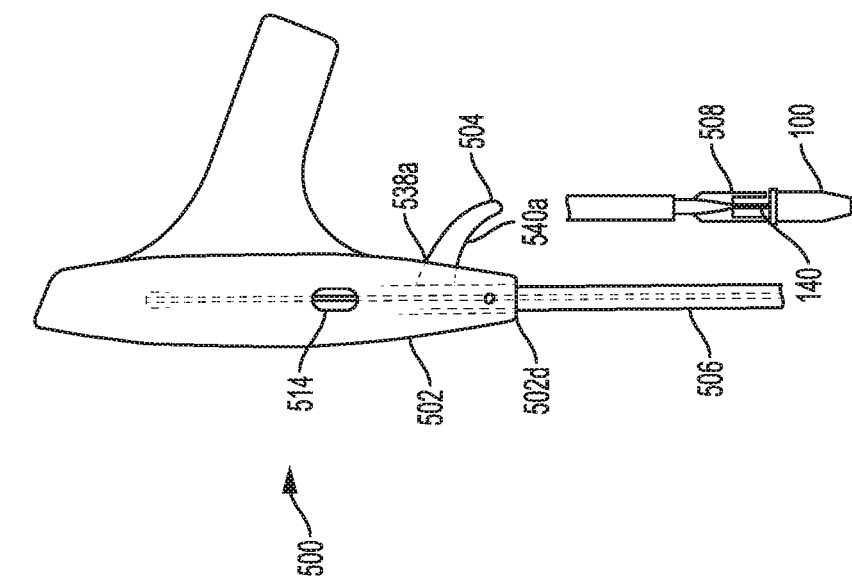
FIG. 3C is a side view of the sheath inserter tool of FIG. 3B, showing an outer shaft retracted from the sheath.

FIGS. 3A-3C show another embodiment of a sheath inserter tool 500 that is similar to the embodiment of FIGS. 2A-2C, but that has a pistol-grip handle assembly. As shown, the tool 500 generally includes a handle 502, an actuator 504 slidably disposed within and extending through the handle 502, and an outer shaft 506 coupled to the actuator 504 and extending within and distally from the handle 502. The outer shaft 506 can include the fork on the distal end thereof, as previously described above with respect to FIGS. 1A-1C.

The handle 502 has a generally elongate cylindrical configuration with a pistol-grip portion to facilitate grasping thereof. The handle 502 can have a blind bore extending therein from the distal end 502d and terminating just distal to the proximal-most end. The bore can be configured to receive the guidewire mated to the sheath, as shown, and a distal portion of the bore can receive the proximal end of the outer shaft 506 for mating the shaft to the actuator. The handle 502 can further include an elongate longitudinal cut-out 538a formed in a sidewall thereof and in communication with the inner lumen. The cut-out 538a can allow the actuator 504 on the inner component to extend therethrough and to slidably move there along.

The actuator 504 is generally trigger-shaped and includes a distal facing finger-gripping surface 540a. The actuator 504 extends laterally outward from a side of the handle 502, and thus allows a user to place the pistol-grip portion of the handle 502 in their palm and to grasp the actuator 504 with one or two fingers to pull the actuator 504 proximally towards the pistol-grip portion of the handle 502. The actuator can thus slide proximally and distally relative to the handle. The actuator 504 can be fixedly mated to or integrally formed on the proximal end of the outer shaft 506. As a result, after the lock 514 is released, movement of the actuator 504 relative to the handle 502 moves the outer shaft 506 relative to the handle 502 and to the guidewire coupled to the sheath 100.

As shown in FIGS. 3A-3C, the handle 502 includes a lock 514 disposed thereon that is similar to the lock 414 of FIGS. 2A-2C. The lock 514 can be moved into a locked position by pushing the lock 514 into the handle 502. When in a locked position as shown in FIG. 3B, the lock 514 prevents proximal movement of the actuator 504 and locks the outer shaft 506 from moving longitudinally with respect to the handle 502. In order to move the actuator 504 and the outer shaft 506 proximally relative to the handle 502 and the guidewire, the lock 514 must be moved to an unlocked position. This can be achieved by pressing the lock 514 so that it moves out and no longer blocks movement of the actuator 504. Proximal movement of the actuator 504 will retract the fork 508 from the sheath 100, as shown in FIG. 3C.

Figure 4B:
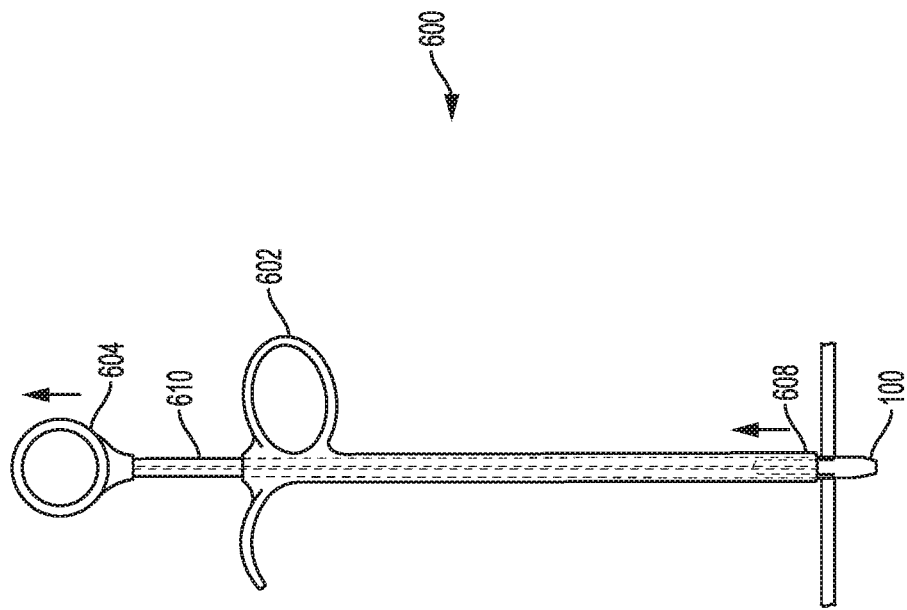
FIG. 4B is a side view of the sheath inserter tool of FIG. 4A, showing an inner shaft of the device retracted from the sheath.
Figure 4A:
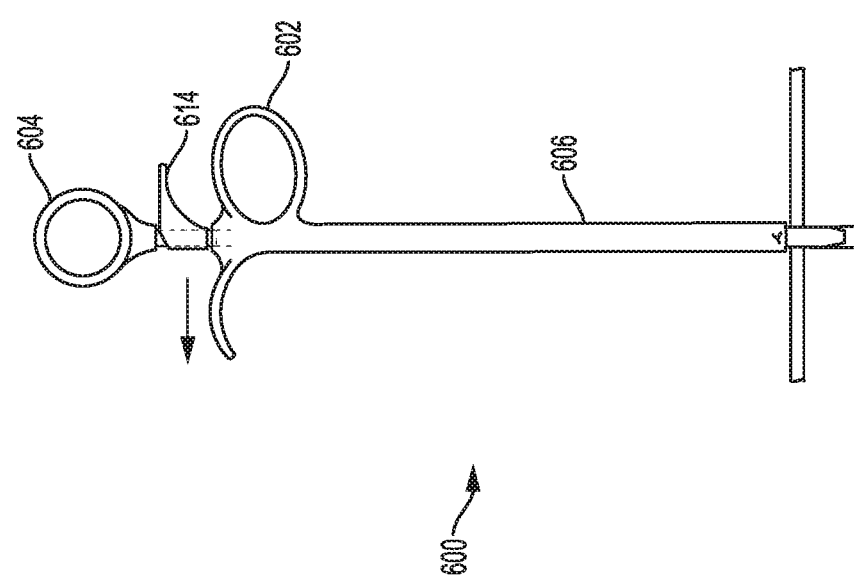
FIG. 4A is a side view of another embodiment of a sheath inserter tool, showing a sheath coupled to the device and being implanted in a bone hole.

FIGS. 4A-4B show another embodiment of a sheath inserter tool 600. In this embodiment, rather than having an outer shaft with a fork that is moved proximally relative to the guidewire coupled to the sheath, the tool 600 includes an inner component having the fork thereon, and the inner component is moved proximally relative to an outer component and the guidewire. In particular, the tool 600 includes an outer component having a handle 602 with an outer shaft 606 extending distally therefrom, and an inner component that includes an actuator 604 in the form of a finger loop that is coupled to a proximal end of an inner shaft 610 that extends through the handle 602 the outer shaft 606. Movement of the inner shaft relative to the outer shaft is effective to move the fork between an extended position, in which the fork extends beyond a distal end of the outer shaft, and a retracted position, in which the fork is retracted into the outer shaft. Once the sheath is positioned in the bone hole, the lock 614 can be released and the fork can be retracted from the sheath. The distal end of the outer shaft 606 can abut the proximal end of the sheath 100 to maintain the sheath within the bone hole.

The handle 602 in this embodiment has a generally T-shaped configuration with one side being in the form of a finger loop and the other side being in the form of a half-loop having a generally elongated arced shaped. This configuration allows a user to rest one finger, e.g., their pointer finger, against the half-loop, and to insert another finger, e.g., their middle finger, through the finger loop. The finger loop and half-loop that form the handle 602 can be integrally formed on or fixedly mated to a proximal end of the outer shaft 602. Both the outer shaft and the handle 602 can include a central lumen extending therethrough for slidably receiving the inner shaft 610.

The actuator 604, which is positioned proximal to the handle 602 and which is coupled to the inner shaft 610, is generally loop-shaped and is configured to receive, for example, a user's thumb. The actuator 604 can be fixedly mated to or integrally formed on the proximal end of the inner shaft 610. As a result, movement of the actuator 604 relative to the handle 602 moves the inner shaft 610 relative to the outer shaft 606.

As shown in FIGS. 4A-4B, the tool 600 can also include a lock 614 for locking the inner and outer shafts 610, 606 in a fixed position relative to one another. In one embodiment, the lock 614 can be in the form of a removable structure that can be snapped onto the inner shaft 610 and that can also engage a flange or other feature (not shown) formed on a proximal end of the handle 602. When the lock 614 is mated to the inner shaft 610 and the handle 602, the inner and outer shafts 610, 606 are prevented from longitudinal movement. The device can be inserted through tissue or through a cannula in the locked position, and once the sheath is implanted within a bone hole, the lock 614 can be removed by moving the lock 614 laterally away from the device 600. With the lock removed, as shown in FIG. 4B, the actuator 604 and the inner shaft 610 can be moved proximally away from the handle 602 and outer shaft 610, thereby retracting the fork 608 out of the sheath 100 and into the outer shaft 606. The outer shaft 606 can remain in position, pressing the sheath into the bone hole.

Figure 5B:
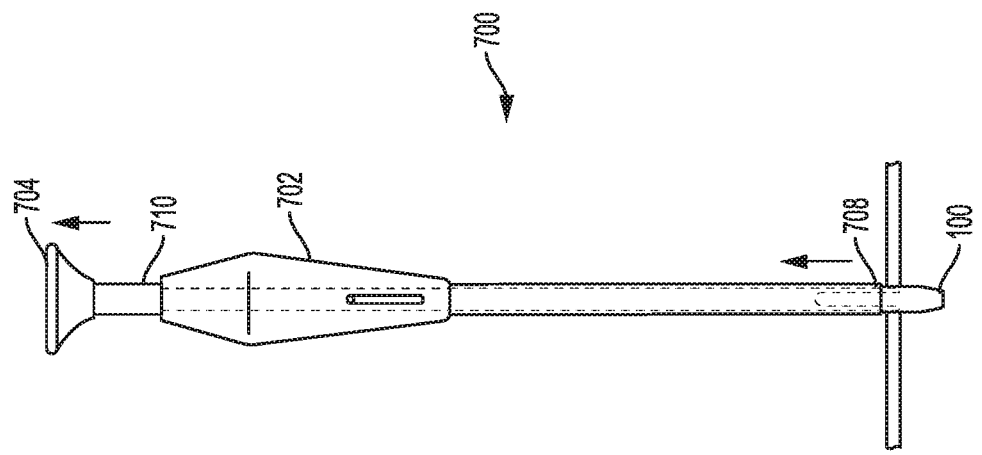
FIG. 5B is a side view of the sheath inserter tool of FIG. 5A, showing an inner shaft of the device retracted from the sheath.
Figure 5A:
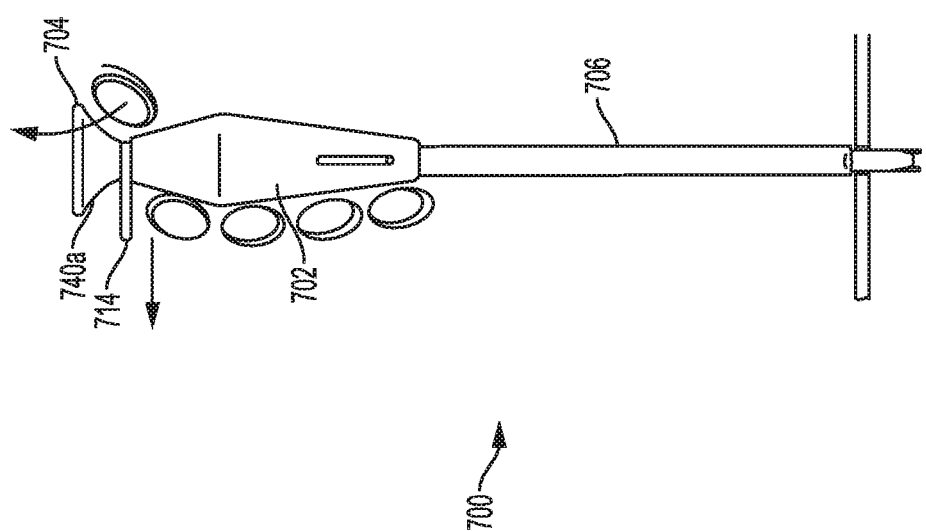
FIG. 5A is a side view of another embodiment of a sheath inserter tool, showing a sheath coupled to the device and being implanted in a bone hole, with circles representing figure positions.

FIGS. 5A-B show another embodiment of a sheath inserter tool 700 that functions in a similar manner to the tool of FIGS. 4A-4B, but that includes a different handle assembly. In particular, the tool 700 includes an outer component having a handle 702 with an outer shaft 706 extending therefrom, and an inner component that includes an actuator 704 that is slidably coupled to an inner shaft 710 extending from the actuator 704 and through the handle 702 and the outer shaft 706.

The handle 702 has a generally elongate cylindrical configuration to facilitate grasping thereof. The diameter can remain constant along the length of the handle 702, or a proximal or the handle can taper inward in a proximal direction, and a distal portion of the handle can taper inward in a distal direction, as shown. The handle 702 can have a bore extending entirely therethrough. The bore can be configured to slidably receive the inner shaft therethrough, and a distal portion of the bore can receive the proximal end of the outer shaft 706 for mating the outer shaft to the handle. Various mating techniques as described above can be used to fixedly mate the outer shaft 706 to the handle 702.

The actuator 704 in this embodiment has a conical shape that tapers inward in a distal direction to form a distal facing finger-gripping surface 740a. The actuator 704 is positioned proximal of the handle 702 to thus allow a user to wrap their fingers around the handle, as indicated by the circles, and to place their thumb in the finger-gripping surface 740a to push the actuator 704 proximally upwards away from the handle 702. The actuator can thus slide proximally and distally relative to the handle 702. The actuator 704 can be fixedly mated to or integrally formed on the proximal end of the inner shaft 710. As a result, movement of the actuator 704 relative to the handle 702 moves the inner shaft 710 relative to the outer shaft 706.

As shown in FIGS. 5A-5B, the device 700 further includes a lock 714 disposed on the inner shaft 710 and configured to engage the proximal portion of the handle 702. While not shown, the handle 702 can include a flange or other feature that is engaged by the lock 714 so as to allow the lock 714 to prevent movement of the inner shaft 710 and the handle relative to one another. The lock 714 can alternatively engage the actuator 704, rather than the inner shaft 710, to prevent movement of the inner and outer components relative to one another. When in a locked position as shown in FIG. 5A, the lock 714 prevents proximal movement of the actuator 704 and locks the inner and outer shafts 710, 706 from moving longitudinally with respect to each other. In order to move the actuator 704 and the inner shaft 710 proximally relative to the handle 702 and outer shaft 710, and to thereby retract the fork 708 from within the sheath 100, the lock 714 can be removed from the device, as can be seen in FIG. 5B.

Figure 6A:
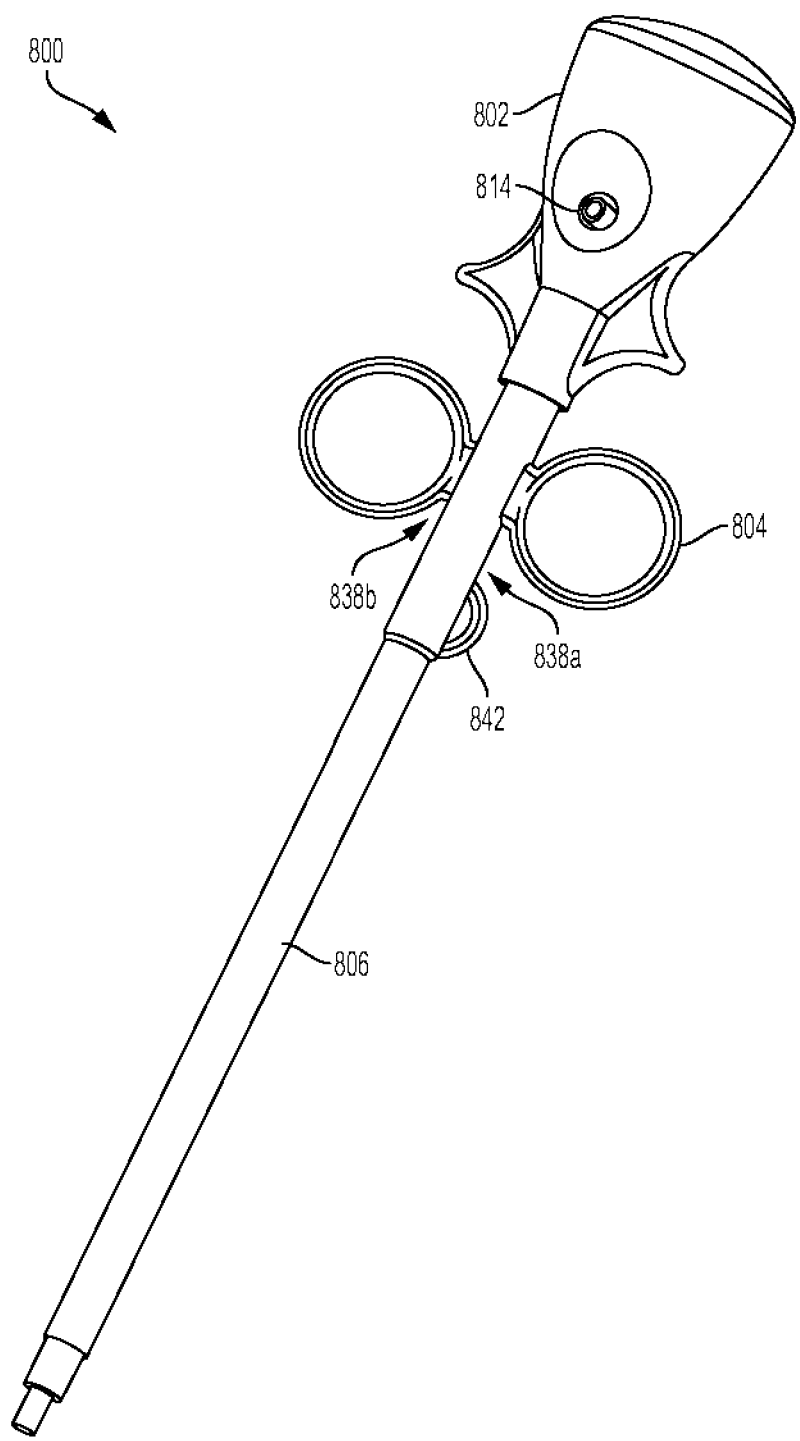
FIG. 6A is a perspective view of another embodiment of a sheath inserter tool.
Figure 6B:
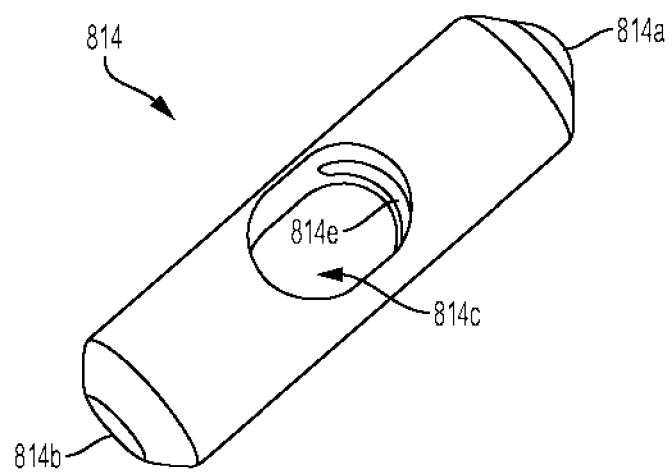
FIG. 6B is side perspective view of a shaft locking mechanism of the tool of FIG. 6A.
Figure 6C:
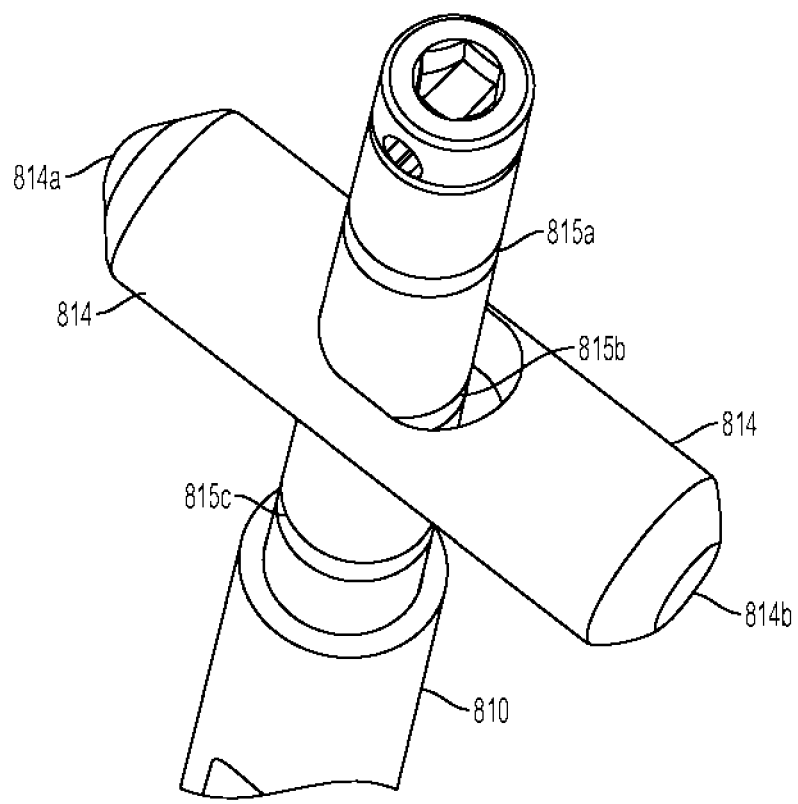
FIG. 6C is a perspective view of the shaft locking mechanism of FIG. 6B shown disposed on the inner shaft of the sheath inserter tool of FIG. 6A.
Figure 6D:
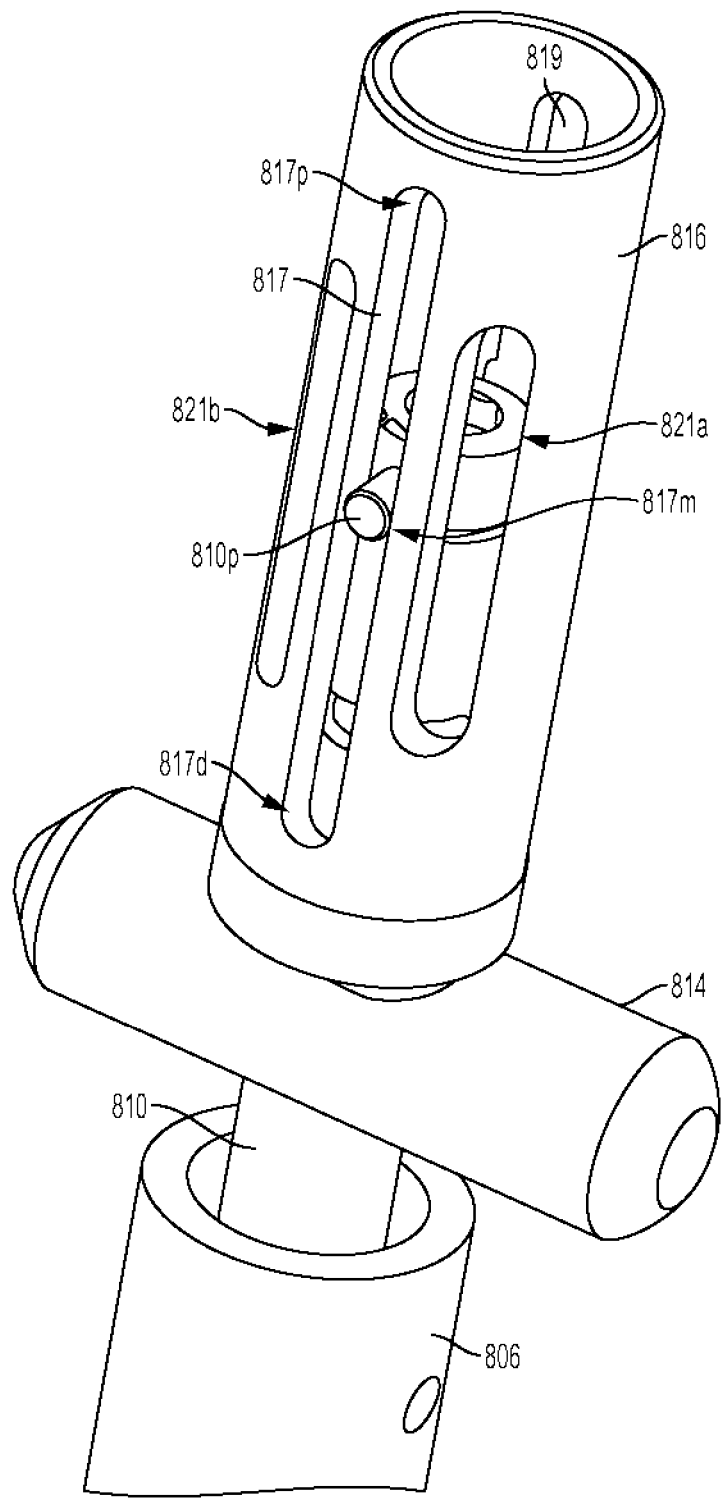
FIG. 6D is a perspective view of portions of the sheath inserter tool of FIG. 6A showing features for hindering movement of the inner shaft relative to the outer shaft.
Figure 6E:
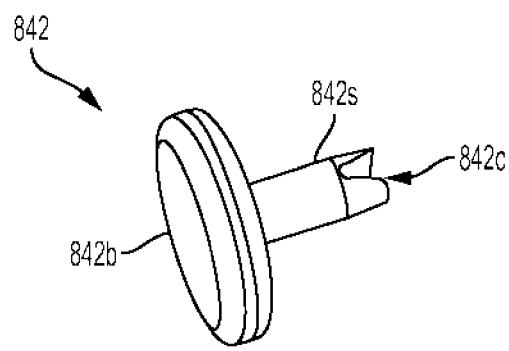
FIG. 6E is a perspective view of a guidewire locking mechanism of the sheath inserter tool of FIG. 6A.
Figure 6F:
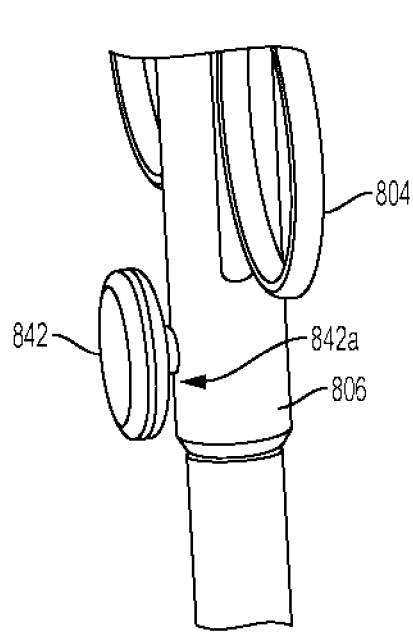
FIG. 6F is a perspective view of the guidewire locking mechanism of FIG. 6E shown mounted on the sheath inserter tool of FIG. 6A.
Figure 6G:
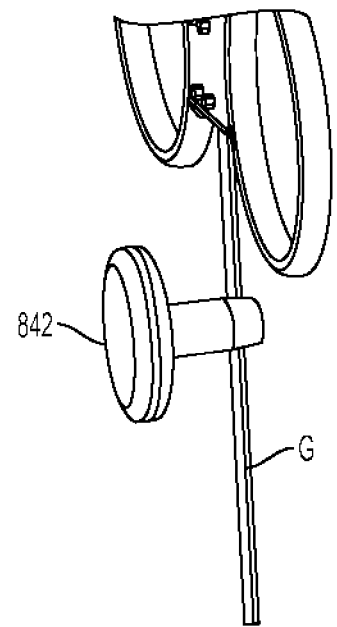
FIG. 6G is a perspective view of the guidewire locking mechanism of FIG. 6E shown engaging a guidewire of the sheath inserter tool of FIG. 6A.
Figure 7:
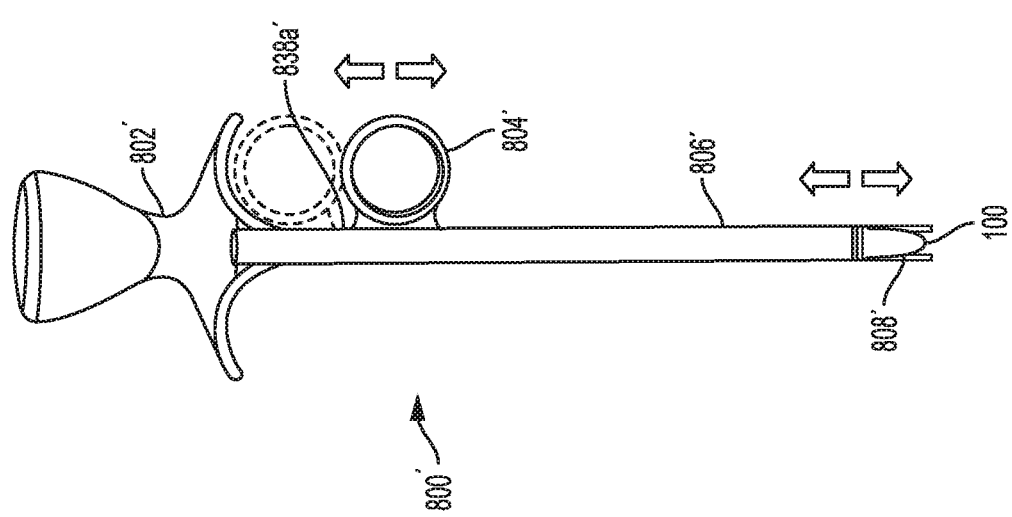
FIG. 7 is a side view of another embodiment of a sheath inserter tool.

FIGS. 6A and 7 show two additional embodiments of sheath inserter tools 800, 800', each of which includes an outer component having a handle 802, 802' with an outer shaft 806, 806' extending distally therefrom, and an inner component that includes an actuator 804, 804' that is positioned distal of the handle 802, 802' and that is mated to or integrally formed on the inner shaft 810, 810'. The actuator 804, 804' can extend through longitudinal slots in the outer shaft 806, 806', and the inner shaft 810 can be slidably disposed within the outer shaft 806, 806'. While not described in detail, a person skilled in the art will appreciate that the tools of FIGS. 6 and 7 can function as previously described with respect to FIGS. 4A-4B.

Each handle 802, 802' can have a generally conical, knob-like configuration for allowing the handle to sit within a user's palm. The handles 802, 802' can include distal-facing recesses formed therein that are configured to seat the finger loop or loops on the actuator, as will be discussed below. Each handle 802, 802' can also have a blind bore extending therein from the distal end and terminating at a location distal to the proximal-most end. The bore can be configured to receive and releasably mate to a guidewire, as described above with respect to FIGS. 1A-1C. A distal portion of the bore can receive the proximal end of the outer shaft 806 for mating the shaft to the handle. The outer shaft 806 can further include two elongate longitudinal cut-outs 838a, 838b, as shown in FIG. 6A, or only a single cut-out 838a' as shown in FIG. 7, formed in the sidewall thereof and in communication with the inner lumen. The cut-outs 838a, 838b, 838a' can allow the actuator 804 on the inner component to extend therethrough and to slidably move there along.

The actuator 804 in FIG. 6A has first and second finger loops for receiving a user's fingers, e.g., the pointer and middle fingers. The actuator 804' in FIG. 7 only has a single finger loop for receiving a single finger, e.g., a pointer finger or thumb. Each actuator 804, 804' extends laterally outward from a sidewall of the outer shaft 806, 806', and thus allows a user to place the proximal end of the handle 802, 802' in their palm and to grasp the actuator 804, 804' with one or more fingers to pull the actuator 804, 804' proximally. The actuator can thus slide proximally and distally relative to the handle. The actuator 804, 804' can be fixedly mated to or integrally formed on a proximal portion of the inner shaft 810, 810'. Preferably, the inner shaft 810 810' extends proximally beyond the actuator to allow the proximal end of the inner shaft to extend into the handle 802 and to be engaged by the lock 814, discussed below. In use, movement of the actuator 804, 804' relative to the handle 802, 802' moves the inner shaft 810, 810' relative to the outer shaft 806, 806' and relative to a guidewire coupled to the handle 802, 802'.

Each tool can further include a lock 814 extending through the handle 802, as seen in FIG. 6A. While only FIG. 6A illustrates a lock, a person skilled in the art will appreciate that the tool of FIG. 7 can likewise include a lock. The lock 814 is shown in more detail in FIGS. 6B-6D, and is generally in the form of an elongate member having a central opening or elongate cut-out 814c formed therein. As shown in FIG. 6B, the cut-out 814c can include an engagement feature 814e, such as a protrusion or ledge, that is configured to be moved in and out of one or more grooves formed in the proximal end of the inner shaft 810. In an exemplary embodiment, as shown, one end of the lock 814 can include a bump 814a formed therein and the other end of the lock 814 can include a recess 814b formed therein. The engagement feature 814e can be formed within the cut-out 814c at a location adjacent to the bump 814a, such that the bump 814a can indicate the closed positioned, whereas the recess 814b can indicate the open position, as will be discussed in more detail below. As shown in FIG. 6C, the proximal end of the inner shaft 810 can include three grooves 815a, 815b, 815c formed therein and spaced longitudinally there along. The proximal-most groove 815a can correspond to a position in which the inner shaft 810 is fully extended relative to the outer shaft 806, the distal-most groove 815c can correspond to a position in which the inner shaft 810 is fully retracted relative to the outer shaft 806, and the middle groove 815b can correspond to a mid-position between the fully extended and fully retracted positions. A person skilled in the art will appreciate that the inner shaft 810 can include any number of grooves formed therein as may be desired. FIG. 6C illustrates the lock 814 engaged in the middle position with the middle groove 815b, with the bump 814a positioned closer to the inner shaft 810 than the recess 814b. The inner shaft 810 is thus preventing from moving relative to the outer shaft 806. Pressing on the recess 814b to slide the lock 814 relative to the handle 802 will move the engagement feature 814e out of engagement with the groove 815b, thus allowing free slidable movement of the inner shaft 810 relative to the outer shaft 806.

As shown in FIG. 6D, the inner shaft can also include features that resist movement of the inner shaft relative to the outer shaft when the lock 814 is disengaged. Such features can also include the position of the inner shaft relative to the proximal-most, middle, and distal-most positions as defined by the grooves 815a-c. In the illustrated embodiment, a collar 816 is disposed around the proximal end of the inner shaft 806 and it includes opposed elongate slots 817, 819 formed therein. While only slot 817 is discussed, it will be appreciated that slot 819 can include the same features and can function in the same manner. As shown, slot 817 can include a three notches formed therein, a proximal-most notch 817p, a middle notch 817m, and a distal notch 817d. Each notch 81'7p, 817m, 817d can be configured to frictionally engage a pin 810p formed on or coupled to the proximal end of the inner shaft 810, at a location above the grooves 815a-c. The notches can engage the pin to hinder but not prevent movement. Moreover, each notch 81'7p, 817m, 817d can be positioned such that, when the pin 810p is seated therein, the button 814 will be aligned with the corresponding proximal, middle, or distal grooves 815a-c. In order to allow the notches 81'7p, 817m, 817d to engage the pin 810p, the collar 816 can include side slots 821a, 821b formed on opposed sides thereof. The side slots 821a, 821b allow the sidewalls surrounding slot 817 to flex as the pin 810p is moved into a notch 817p, 817m, 817d.

The device can also include a feature for preventing longitudinal movement of the guidewire. FIGS. 6E-6G illustrate a button 842 that is configured to releasably engage the guidewire G extending through the shaft 806. As shown, the button includes a head 842h and shaft 842s extending therefrom. The shaft 842s includes a slot or cut-out 842c formed in the distal end thereof for engaging the guidewire G. The cut-out 842c is configured to snap onto the guidewire G to prevent movement of the guidewire G relative to the button 842. The outer shaft 806 can include an opening 842a formed therein for receiving the button 842. In use, the button 842 can be pressed through the opening 842a to cause the cut-out 842c to engage the guidewire G, and removing the button can release the guidewire G.

Figure 8:
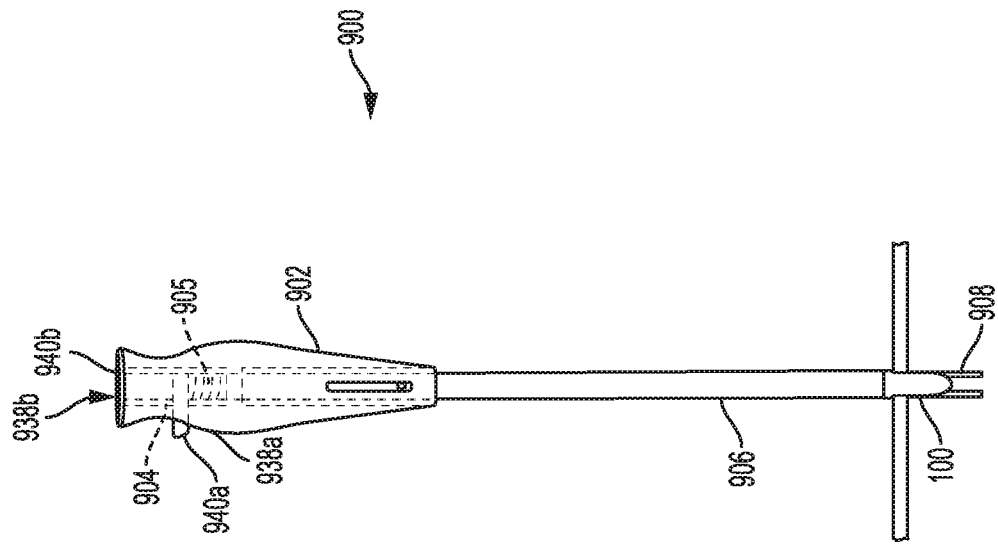
FIG. 8 is a side view of yet another embodiment of a sheath inserter tool.

FIG. 8 shows another embodiment of a sheath inserter tool 900 that functions in a similar manner as described above. In general, the tool includes an outer component having a handle 902 with an outer shaft 906 extending therefrom, and an inner component that includes an actuator 904 that is coupled to the inner shaft 910, which extends through the handle 902 and the outer shaft 906.

The handle 902 has a generally elongate cylindrical configuration to facilitate grasping thereof. The handle 902 can have a bore extending entirely therethrough. The bore can be configured to slidably receive the inner shaft therethrough, and a distal portion of the bore can receive the proximal end of the outer shaft 906 for mating the shaft to the handle. The handle 902 can further include a side cut-out 938a formed in a sidewall thereof and a top cut-out or opening 938b formed in the proximal-most end thereof. The side cut-out 938a can allow a lateral finger grip 940a to extend therethrough, and the top cut-out 938b can allow a proximal finger grip 940b to extend therethrough.

The actuator 904 is generally conical and includes a biasing element 905 (such as a spring) proximal to the inner shaft 910 in the handle 902 that, in a compressed state, results in the fork 908 being in a fully extended position when the sheath 100 is mated to the tool (as shown in FIG. 8). The actuator 904 can be actuated by pressing the lateral finger grip 940a radially inward toward the handle 902 until the surface 940a is within the handle. This radially inward movement causes the biasing element 905 to be released from the compressed state. The release of the biasing element 905 will cause the biasing element 905 to move proximally to an elongated, relaxed state, which will cause the inner shaft 910 to move proximally with respect to the outer shaft 906 and handle 902, thereby retracting the fork 908 from the sheath 100 and into the outer shaft. After first actuation and as the biasing element 905 of the actuator 904 moves to a relaxed state, the movement will cause the proximal finger grip 940b to move proximally relative to the handle 902.

Distal movement of the proximal finger grip 940b can reverse the retraction, causing the biasing element 905 to re-compress by moving the spring distally into a compressed state until the lateral finger grip 940a can again extend through the cut-out 938a. This movement will cause the inner shaft 910 to move distally again. A user can place the elongate cylindrical configuration of the handle 902 in their palm and manipulate the actuator 904 with, for example, a thumb. The actuator 904 can be fixedly mated to or integrally formed on the proximal end of the inner shaft 910. As a result, movement of the actuator 904 relative to the handle 902 moves the inner shaft 910 relative to the outer shaft 906.

Figure 9:
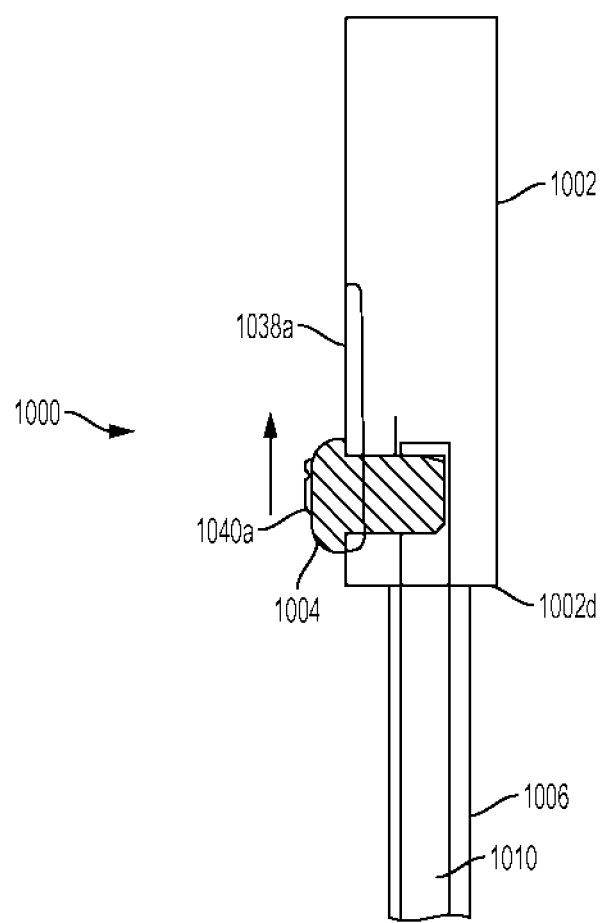
FIG. 9 is a side view of another embodiment of a handle portion of a sheath inserter tool.

FIG. 9 shows a proximal portion of another embodiment of a sheath inserter tool 1000 that can function as previously described with respect to FIGS. 4A-4B. In this embodiment, the tool 1000 includes an outer component having a handle 1002 with an outer shaft 1006 extending therefrom, and an inner component that includes an actuator 1004 that is slidably disposed relative to the handle 1002 and that is coupled to an inner shaft 1010 extending through the handle and through the outer shaft 1006. While not shown, the distal end can be similar to the aforementioned embodiments, with the inner shaft including a fork thereon as described with respect to FIGS. 1A-1C.

The handle 1002 has a generally elongate cylindrical configuration to facilitate grasping thereof. The handle 1002 can have a blind bore extending therethrough from the distal end 1002d and terminating just distal to the proximal-most end. The bore can be configured to receive a proximal end of a guidewire mated to a sheath. While not shown, the bore can include a guidewire grasper for releasably engaging the guidewire, as discussed above. A distal portion of the bore can receive the proximal end of the outer shaft 1006 for mating the shaft to the handle. The handle 1002 can further include an elongate longitudinal cut-out 1038a formed in a sidewall thereof and in communication with the inner lumen. The cut-out 1038a can allow the actuator 1004 on the inner component to extend therethrough and to slidably move there along.

The actuator 1004 is in the form of a sliding button or knob that includes a finger-gripping surface 1040a. The actuator 1004 extends laterally outward from a side of the handle 1002, and thus allows a user to place the handle 1002 in their palm and to manipulate the actuator 1004 with fingers, for example a thumb, to move the actuator 1004 proximally and distally relative to the handle. The actuator 1004 can be fixedly mated to or integrally formed on the proximal end of the inner shaft 1010. As a result, movement of the actuator 1004 relative to the handle 1002 moves the inner shaft 1010 relative to the outer shaft 1006, thereby retracting a fork on the distal end of the inner shaft from a sheath (not shown) and into a distal end of the outer shaft. Similar to the other embodiments, the handle 1002 can also include a lock (not shown).

Figure 10B:
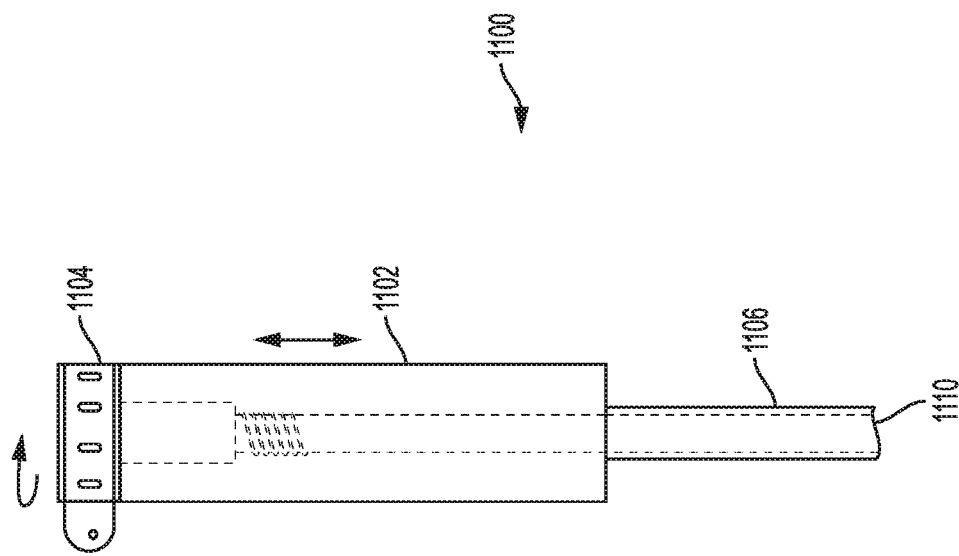
FIG. 10B is an enlarged side view of a handle portion of the sheath inserter tool of FIG. 10A.
Figure 10A:
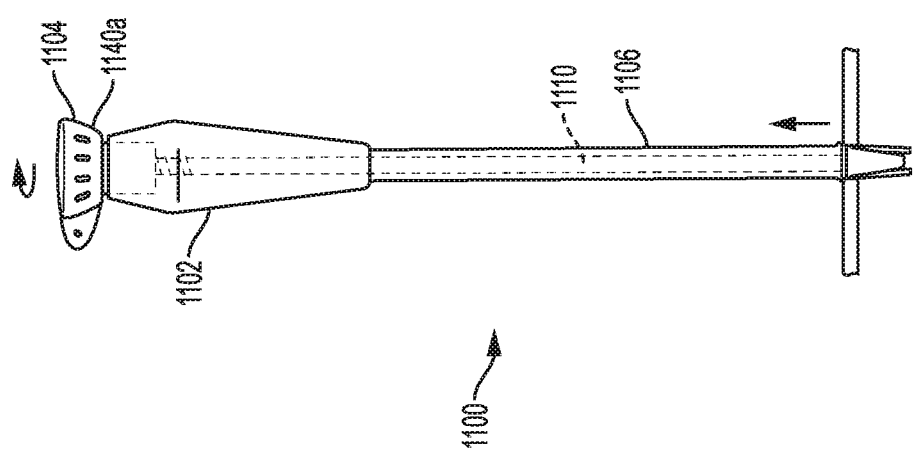
FIG. 10A is a side view of another embodiment of a sheath inserter tool having a rotating actuator.

FIGS. 10A-10B show another embodiment of a sheath inserter tool 1100 that functions in a similar manner to the aforementioned embodiments, and that generally includes an outer component having a handle 1102 with an outer shaft 1106 extending therefrom, and an inner component that includes an actuator 1104 that is positioned proximal to the handle 1102 and that is coupled to a proximal end of an inner shaft 1110 extending through the handle 1102 and through the outer shaft 1106.

The handle 1102 has a generally elongate cylindrical configuration to facilitate grasping thereof. The handle 1102 can have a bore extending entirely therethrough for receiving the inner shaft. A distal portion of the bore can receive the proximal end of the outer shaft 1106 for mating the shaft to the handle. The bore can allow the actuator 1104, or a portion thereof, on the inner component to extend therethrough and to rotatably move thereabove.

The actuator 1104 is generally disc-shaped and includes a finger-gripping surface 1140a. The actuator 1104 is positioned at a proximal end of the handle 1102, and thus allows a user to place the elongate cylindrical configuration of the handle 1102 in their palm and to manipulate the actuator 1104 with, for example, a thumb to rotate the actuator 1104 relative to the handle 1102. The actuator 1104 can be threadably mated to the proximal end of the inner shaft 1110. In particular, the actuator 1104 can include a cylindrical shaft extending longitudinally from the disc-shaped portion and having threads formed therein that are configured to mate with threads on a proximal end of the inner shaft. The actuator 1104 can be coupled to the handle 1102 such that it is freely rotatable, but is prevented from moving axially. As a result, rotation of the actuator 1104 relative to the handle 1102 moves the inner shaft 1110 relative to the outer shaft 1106. Rotation of the actuator 1104 can thus cause proximal movement of the inner shaft 1110 relative to the handle 1102 and outer shaft 1110 to thereby retract a fork on the inner shaft from a sheath and into the outer shaft. Similar to the other embodiments, the handle 1102 can also include a lock (not shown). The lock can be incorporated into the actuator 1104, for example by using ball and detents that retain the actuator 1104 in one or more positions.

FIGS. 11A-11C show another embodiment of a sheath inserter tool 1200 having an outer component with a handle 1202 with an outer shaft 1206 extending distally therefrom, and an inner component that includes an actuator 1204 that is pivotably coupled to the handle 1202 and that is coupled to an inner shaft 1210 extending through the outer shaft 1206. The tool functions in a similar manner as described above with respect to FIGS. 4A-4B, with the inner shaft having a fork on a distal end thereof that is movable between extended and retracted positions.

The handle 1202 in this embodiment has a generally elongate cylindrical configuration to facilitate grasping thereof. The handle 1202 can have a blind bore extending therethrough from the distal end 1202*d* and terminating just distal to the proximal-most end. The bore can be configured to receive a guidewire coupled to the sheath, and it can optionally include components for releasably engaging the guidewire. A distal portion of the bore can receive the proximal end of the outer shaft 1206 for mating the shaft to the handle.

The actuator 1204 in this embodiment is generally lever-shaped and includes finger-gripping surface 1240*a*. The actuator 1204 is pivotably attached to the handle 1202 and extends laterally outward in a resting position from a side of the handle 1202, as shown in FIG. 11A. This allows a user to place the handle 1202 in their palm and to manipulate the actuator 1204 with their fingers (as indicated by the circles) to squeeze and pivotally move the actuator 1204 toward the handle 1202. A linkage 1207 extends from a proximal end of the actuator 1204 and is coupled to a distal end of a biasing element, e.g., a spring 1209 located inside the handle 1202. The spring is positioned proximal to the inner shaft 1210 and is coupled to the inner shaft 1210. At rest, the biasing element of the actuator 1204 causes the fork 1208 on the inner shaft to be in a fully extended position, extending from the outer shaft 1206. In FIG. 11C, upon pivotal movement of the actuator 1204 relative to the handle 1202, the linkage causes the spring to compress proximally, thereby moving the inner shaft proximally relative to the outer shaft 1206 to retract the fork 1208 into the outer shaft. Similar to the other embodiments, the handle 1202 can also include a lock (not shown) which can be separate from or incorporated into the actuator 1204.

A person skilled in the art will appreciate that the various tools discussed above can have a variety of configurations. For example, while tools are described having a handle with a bore that receives a proximal end of the outer shaft, in each of these embodiments the handle can be integrally formed on the outer shaft or the outer shaft can be mated to a distal facing surface of the handle without the need to extend into the handle. Other similar modifications can be made as needed to connect the various components.

Figure 14:
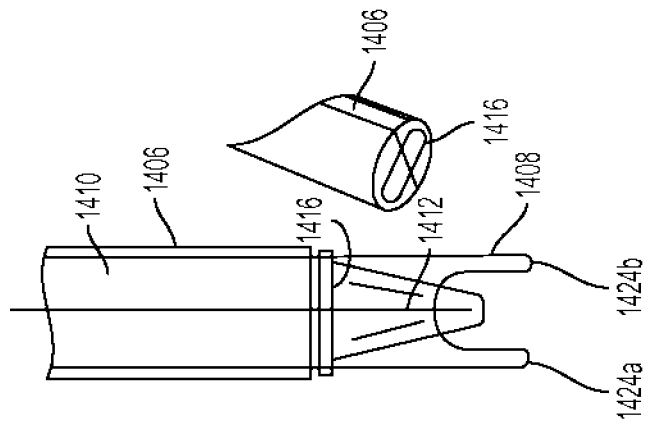
FIG. 14 is a side and perspective view of another embodiment of a sheath alignment feature.
Figure 13:
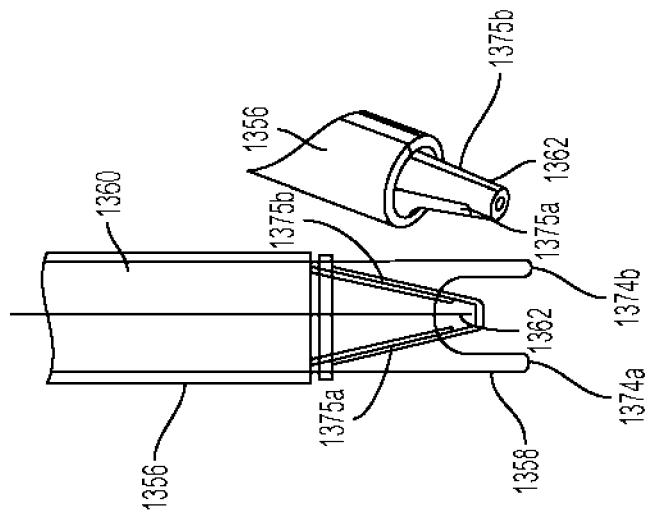
FIG. 13 is a side view and perspective of another embodiment of a sheath alignment feature.
Figure 12:
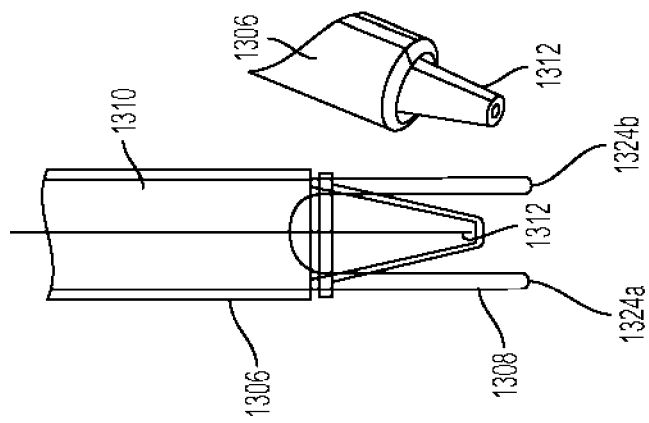
FIG. 12 is a side and perspective view of one embodiment of a sheath alignment feature.

FIGS. 12-14 show embodiments of a sheath alignment feature that can be included in an inserter tool, including any of the inserter tools discussed above. FIG. 12 shows an outer shaft 1306 and inner shaft 1310. A fork 1308 is formed on or mated to the distal end of the inner shaft 1310, and the fork 1308 includes first and second elongate prongs 1324*a*, 1324*b* extending longitudinally from opposed sides of the inner shaft 1310. The outer shaft 1306 includes a sheath alignment feature 1312 formed on a distal end thereof and having a generally cone-shaped configuration, tapering inward in a distal direction. The shape can be configured to match the shape of an inner lumen or bore in a sheath so as to allow the sheath alignment feature to be received within the sheath when the sheath is mated to the inserter tool. The sheath alignment feature 1312 can further include cut-outs or openings formed in opposed sides adjacent to the proximal end for receiving the prongs therethrough. The sheath alignment feature 1312 can have a proximal portion having a diameter that is smaller than the diameter of the distal end of inner shaft. This allows the first and second elongate prongs 1324*a*, 1324*b* on the inner shaft 1310 to extend through the cut-outs in the sheath alignment feature (or the distal end of the outer shaft) and to extend along opposed sides of the sheath alignment feature 1312. In use, the sheath alignment feature can extend into a sheath coupled to the tool, thereby facilitating alignment of the sheath with respect to the tool. The prongs can extend along the sheath alignment feature and along opposed sidewalls slots in the sheath. An exemplary sheath for use with this configuration of a distal end of an inserter tool is described in more detail in the applications incorporated by reference above.

FIG. 13 shows another embodiment of a sheath alignment feature 1362 that is similar to the embodiment of FIG. 14, but that includes elongate cut-outs formed in opposed sides of the sheath alignment feature 1362. In particular, the inner shaft 1360 includes a fork 1358 first and second elongate prongs 1374*a*, 1374*b* that extend longitudinally along opposed sides of the sheath alignment feature 1362 on the outer shaft 1360. The sheath alignment feature includes first and second opposed cut-outs 1375*a*, 1375*b* formed therein and configured to receive the first and second elongate prongs 1374*a*, 1374*b*.

FIG. 14 shows another embodiment of a distal portion of an insertion tool that is similar to the embodiments of FIGS. 12 and 13, but that includes an elongate slot in the outer shaft 1406 for receiving the forks on the inner shaft 1410. In particular, the distal end of the outer shaft 1406 is closed with an elongate slot 1416 formed therein. The elongate slot is dimensioned and configured for receiving first and second prongs 1424*a*, 1424*b* of fork 1408 such that the first and second prongs 1424*a*, 1424*b* can extend distally from the distal end of inner shaft 1410, as with other embodiments. Moreover, in this embodiment a sheath alignment feature 1412 is formed on the fork 1408 between the first and second prongs 1424*a*, 1424*b*. The illustrated sheath alignment feature 1412 has a generally cone-shaped configuration, tapering inward in a distal direction.

Figure 16:
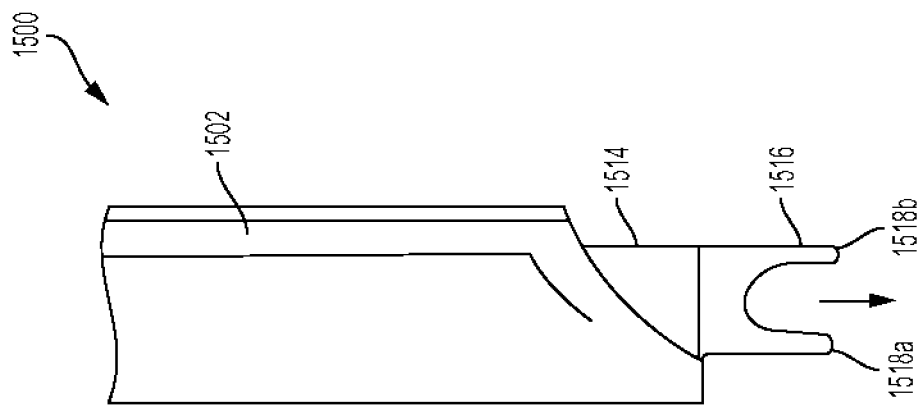
FIG. 16 is a side view of the cannula of FIG. 15, showing a forked inserter extending distally therefrom.
Figure 15:
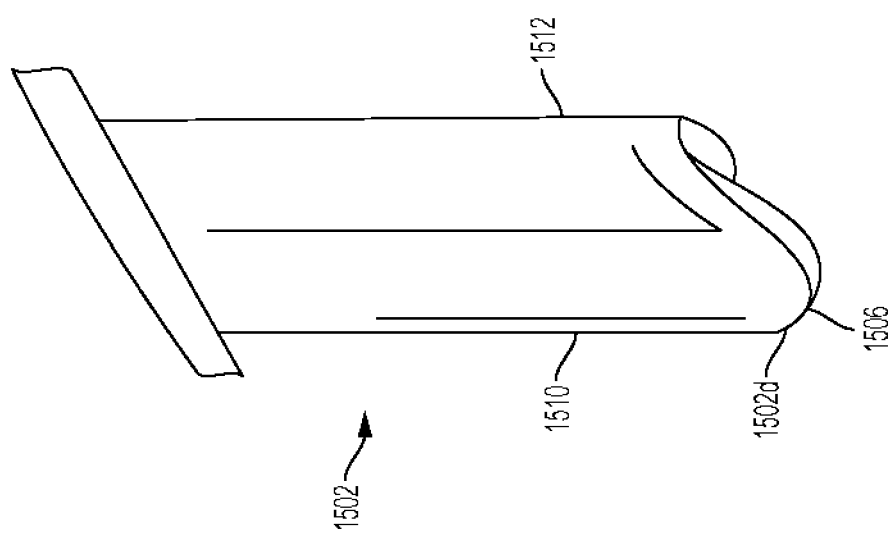
FIG. 15 is a side perspective view of a distal end of one embodiment of a cannula.
Figure 17:
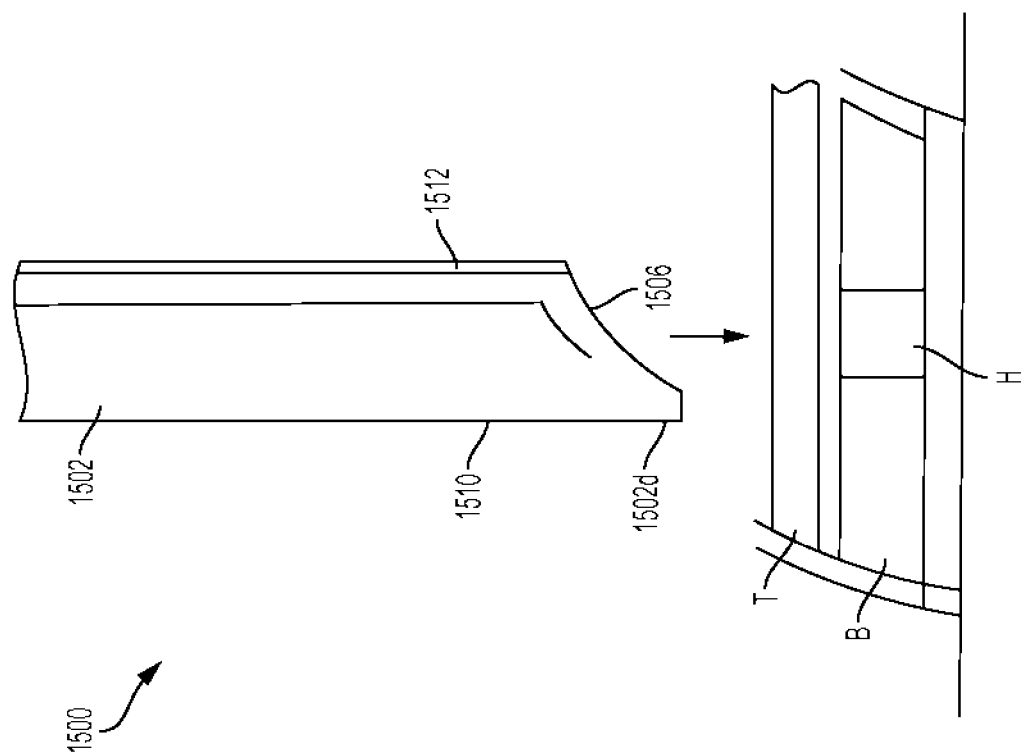
FIG. 17 is a side view of the cannula and forked inserter of FIG. 16 about to anchor a tendon against a bone surface.

FIGS. 15-20 illustrate various tools for maintaining tension on a tendon during anchoring of the tendon. These features can be incorporated into an inserter tool, including any of the inserter tools discussed above, or they can be provided on a separate tool, such as a cannula. FIGS. 15-17 illustrate one embodiment of a tool, in the form of a cannula that includes an outer shaft 1502 having a distal end 1502*d* with a saddled or beveled edge 1506 forming an angled viewing window. The beveled edge 1506 can be rounded and can extend cross-sectionally through the shaft 1502 from a first sidewall 1510 to a second sidewall 1512 on the opposite side of the shaft 1502, such that the first sidewall 1510 extends a distance distally beyond the second sidewall 1512. Such a configuration will result in an opening through the second sidewall 1512 when the cannula 1500 is positioned against tissue and bone, as shown in FIG. 17.

In use, a forked inserter tool 1514 can be passed through the outer shaft 1502 to allow prongs 1518*a*, 1518*b* on the forked distal end 1516 to be used to advance a tendon into a bone hole. The forked inserter tool 1514 can move axially relative to the outer shaft 1502 to retract and extend the prongs 1518*a*, 1518*b* into and from the outer shaft 1502. As shown in FIG. 17, the distal-most end of the outer shaft 1502 can be positioned on a tendon T against bone B to pinch the tendon T to be anchored and thereby prevent slippage of the tendon T. The outer shaft 1502 is preferably positioned on a side of the bone hole H that the tendon extends from, e.g., the distal side of a bone hole on the humerus for a biceps tenodesis procedure. The outer shaft will thus maintain a tension of the tendon T, while the forked inserter tool is extended to push or dunk the tendon into the bone hole. During dunking, the portion of the tendon that is not anchored to the bone by the outer shaft will be pushed into the bone hole. While not shown, the fork can have a sheath loaded thereon that is inserted into the bone hole to maintain the tendon in the bone hole.

Figure 20:
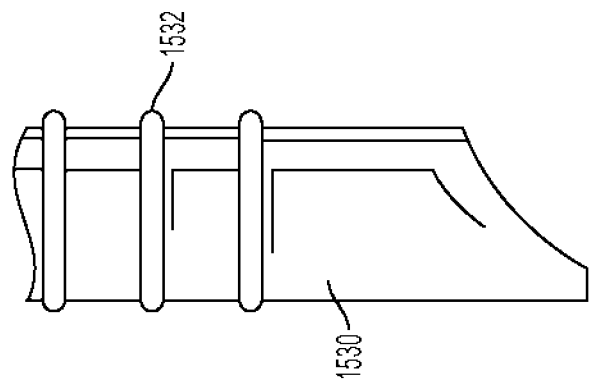
FIG. 20 is side view of the cannula of FIG. 19.
Figure 19:
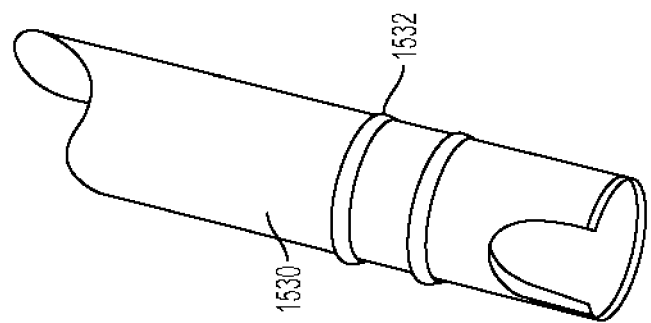
FIG. 19 is a side perspective view of another embodiment of a cannula having ribs formed thereon.
Figure 18:
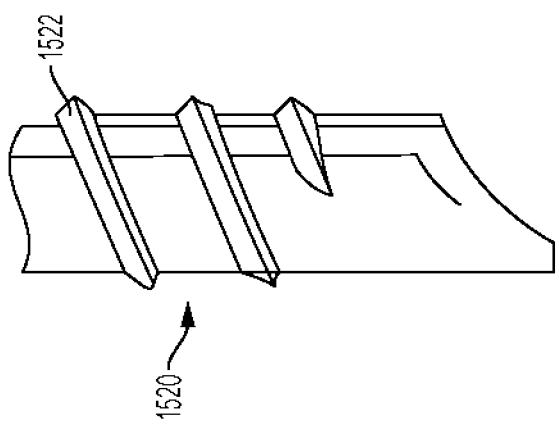
FIG. 18 is a side perspective view of another embodiment of a distal portion of a cannula having threads formed thereon.

In some embodiments, as shown in FIGS. 18-20, the cannula or outer shaft of an inserter tool can include various features formed thereon to resist backout or any unintentional proximal movement of the outer shaft during use. For example, FIG. 18 illustrates threads 1522 formed on an outer shaft 1520 and FIGS. 19 and 20 illustrate ribs 1532 formed on the outer shaft 1530. The threads and ribs can provide resistance against the surrounding tissue to resist any unintentional proximal movement of the outer shaft. In some embodiments, the distal portion of the outer shaft can be free of surface features. In some embodiments, the distal portion of the outer shaft can be formed from a transparent material, can include a compressible material, and/or can have smooth surface.

Figure 22:
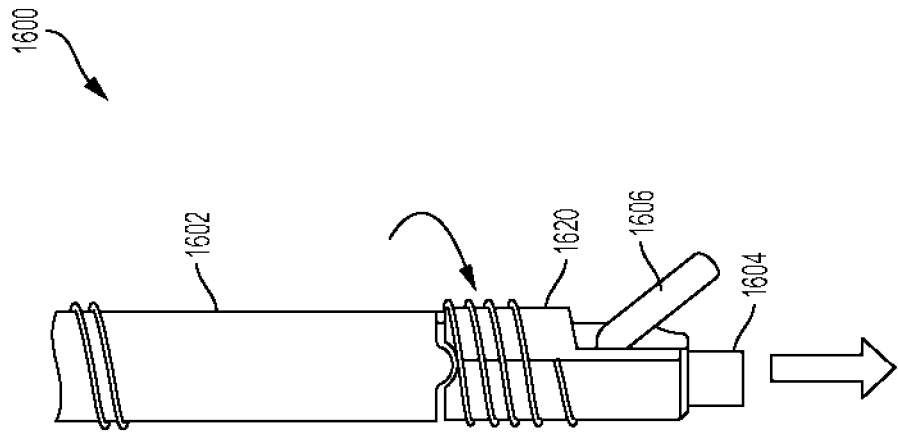
FIG. 22 is a side perspective view of the inserter tool and anchor of FIG. 21 coupled together.
Figure 21:
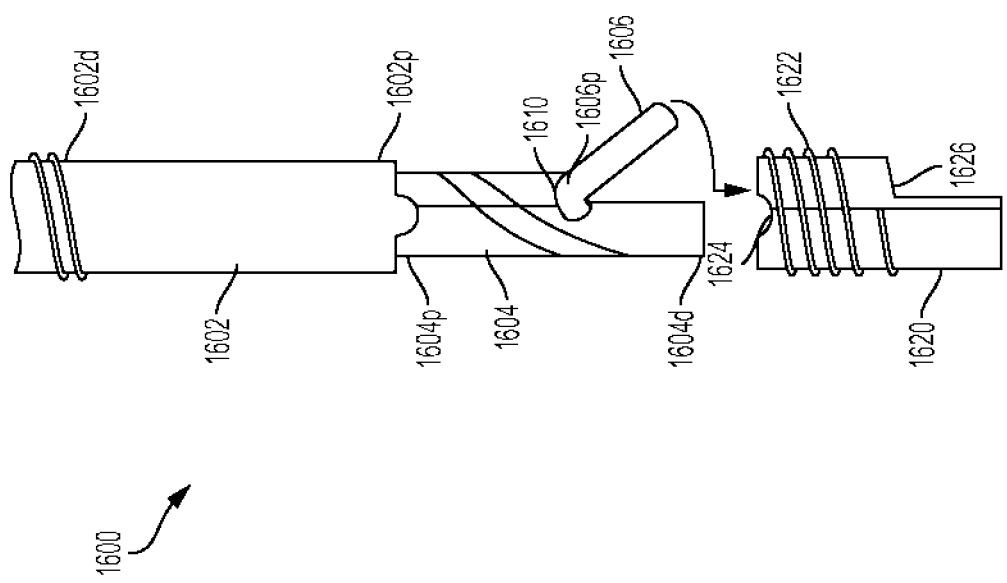
FIG. 21 is a side perspective view a distal portion of another embodiment of a inserter tool and anchor.

In another embodiment, a sheath inserter can include a distal end having movable tendon engagement features. As shown in FIGS. 21-22, an inserter tool 1600 is provided and includes an outer shaft 1602 coupled to a handle as discussed above and an inner shaft 1604 having a tendon engagement member 1606. The tendon engagement member 1606 can be in the form of a pivotable arm having a proximal end that is coupled to the inner shaft 1604 via a hinge 1610 or similar attachment mechanism. The distal end of the tendon engagement member 1606d can move laterally away from and rotate about the axis of the hinge. The distal end of the inner shaft 1604d can be inserted into an anchor 1620. The anchor 1620 can have an inner lumen 1624 to receive the distal end of the inner shaft 1604d, ribs 1622 formed thereon and a recess feature 1626 to receive the tendon engagement feature. As shown in FIG. 22, when the anchor 1620 is coupled to the inserter 1600 the proximal end of the anchor 1620p abuts the distal end of the outer shaft 1602d. The distal end of the inner shaft 1604d can extend through the inner lumen 1624 and past the distal end of the anchor 1620d. The tendon engagement feature 1606 can be advanced and articulated to grab the tendon and pull the tendon proximate to the anchor 1620. The inserter 1600 can then be advanced to position the tendon and the anchor 1620 inside the bone hole. The tension on the tendon is thus maintained by the inserter tool during insertion of the tendon into the bone hole. A person skilled in the art will appreciate that while the anchor 1620 is illustrated with threads formed thereon, the anchor can be non-threaded or can include along only portions or the entire length thereof.

FIGS. 23-31 illustrate various embodiments of a sheath/fork protector that is configured to cover a sheath/fork and optionally a distal portion of a sheath inserter tool during insertion through tissue, and/or that facilitates insertion of the device through tissue. FIG. 23 shows a disposable, thin-walled sheath protector 2105 that effectively covers a sheath 2106, a fork with prongs 2107, and a distal end of an inserter 2108. In this embodiment, the sheath protector 2105 has a generally elongate cylindrical configuration with a conical distal tip. The conical distal tip can function as an obturator to facilitate penetration through tissue percutaneously. The length of the sheath protector can be configured to allow the sheath protector 2105 to extend over a portion of the distal end of the outer shaft. A proximal end of the sheath protector 2105 can include a tab extending radially outward therefrom to facilitate grasping of the sheath protector. In use, the sheath protector is inserted through tissue in the position shown in FIG. 23. The tab on the proximal end can then be grasped and the sheath protector can be slid proximally along the outer shaft to expose the sheath and the distal end of the inserter tool once inserted. To allow such movement, the distal conical portion of the sheath protector can include one or more slits formed therein to allow the distal end to open up and expand around the sheath and outer shaft.

Figure 25:
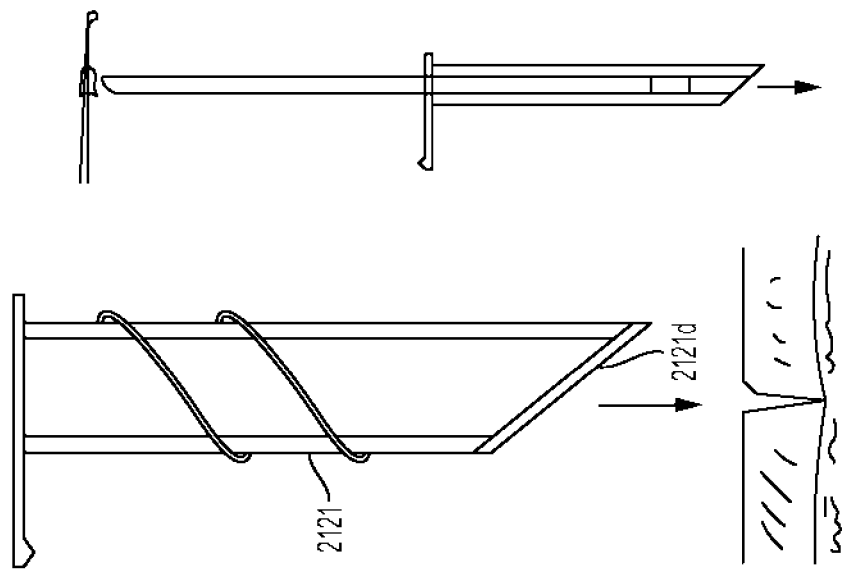
FIG. 25 is a side view of the sheath protector of FIG. 25, shown about to be passed through tissue.
Figure 24:
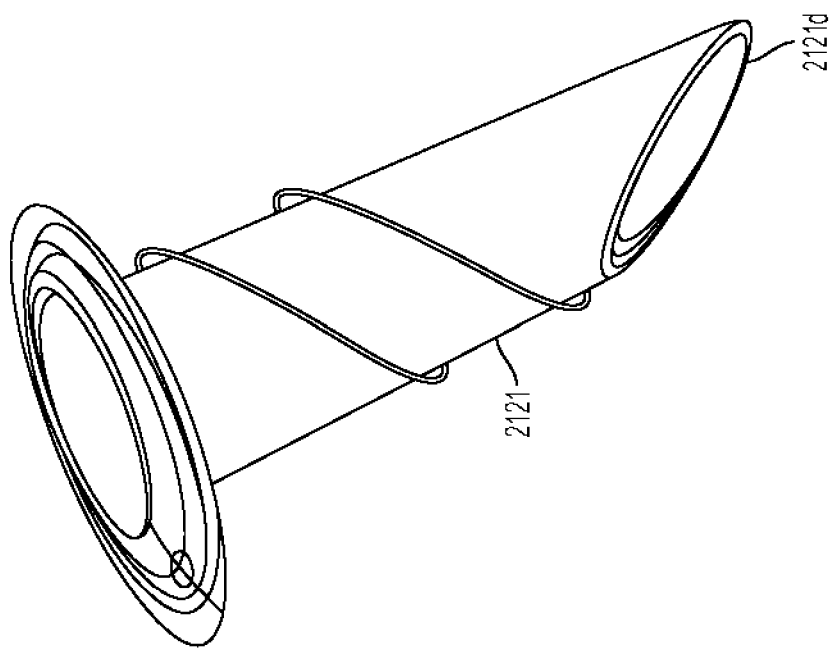
FIG. 24 is a perspective view of another embodiment of a sheath protector.
Figure 26:
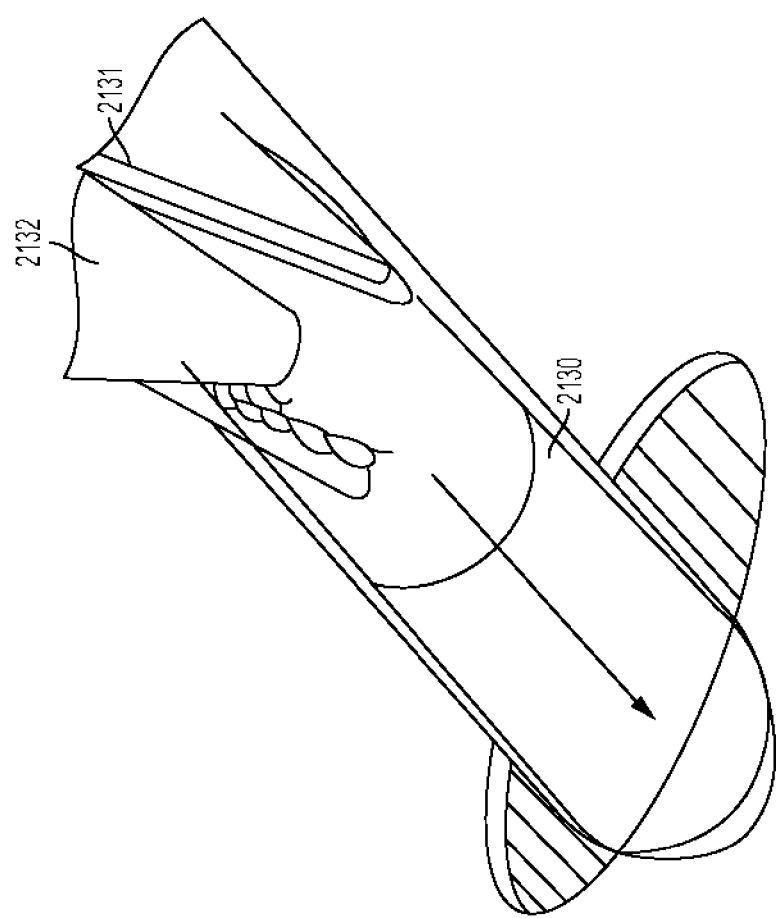
FIG. 26 is a side view of another embodiment of a sheath protector.

FIGS. 24-25 show another embodiment of a sheath protector 2121 with an angled distal tip 2121d, which can assist in accurate insertion in procedures when narrow or small insertion points are required. FIG. 26 shows another embodiment where the sheath protector 2130 has a semi-cylindrical shape and is open along its entire longitudinal length. The sheath protector can be inserted through tissue to provide a pathway or slide for insertion of the sheath/fork. The fork 2131 and sheath 2132 can be introduced by sliding them along the open sheath protector 2130.

Figure 27:
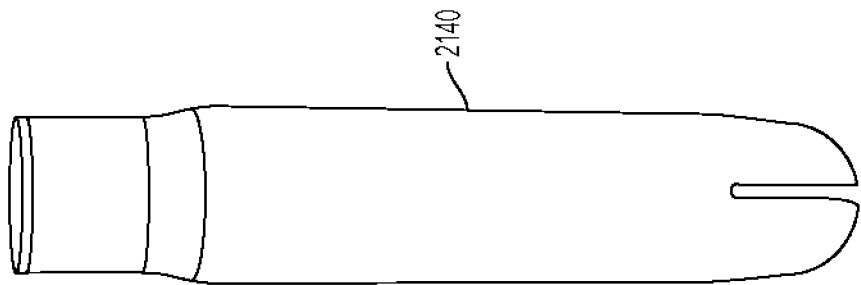
FIG. 27 is a side view of an embodiment of a sheath protector.
Figure 29:
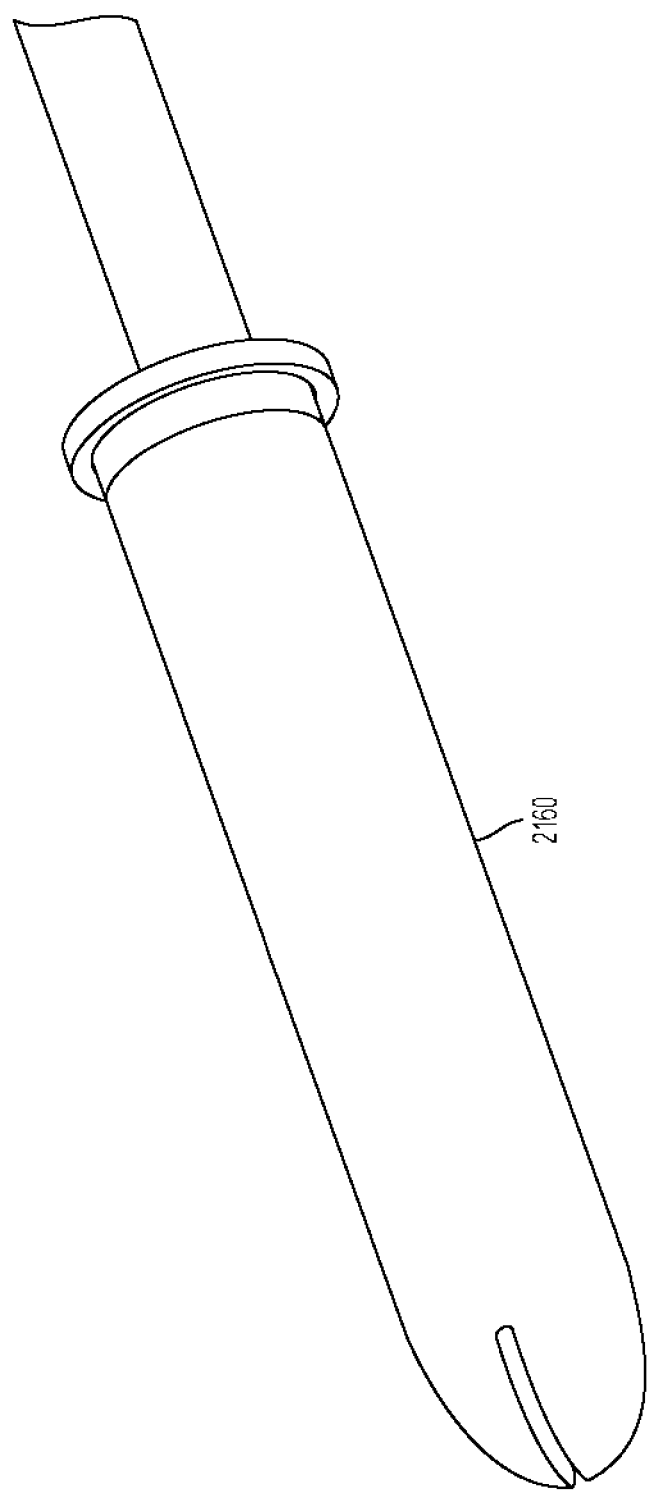
FIG. 29 is a perspective view of the sheath protector of FIG. 28 loaded onto a distal end of a sheath and sheath inserter tool.

FIG. 27 shows another embodiment of a bullet-shaped sheath/fork protector 2140. FIG. 28 shows two sheath/fork protectors 2150, 2151 having different sizes for use with different sized sheaths, and FIG. 29 shows a sheath protector 2160 covering a distal end of an inserter with a sheath. The sheath protectors can be configured with distal tips designed to separate (open and close) upon distal movement of the inserter and sheath.

Figure 30:
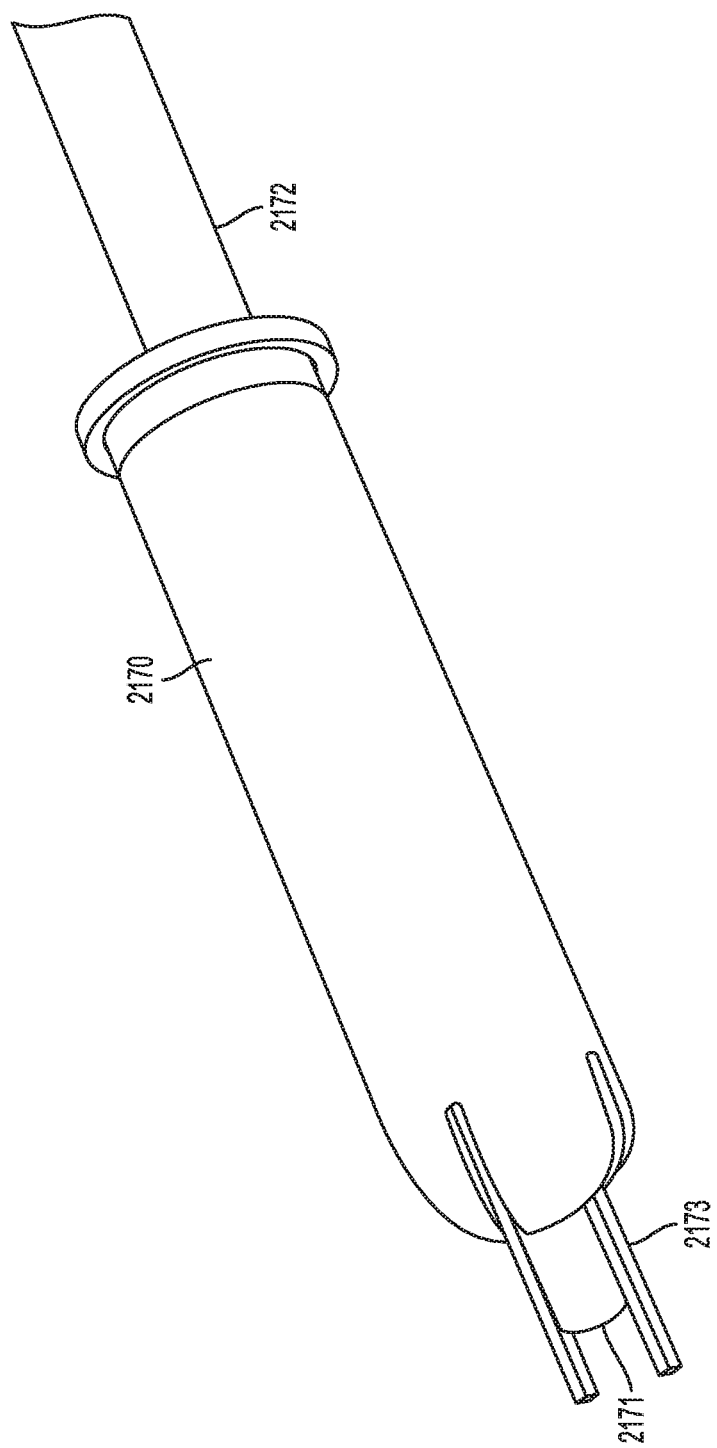
FIG. 30 is another perspective view of the sheath, inserter tool, and sheath protector of FIG. 29 with forks on the sheath inserter tool being passed through the protector.
Figure 31:
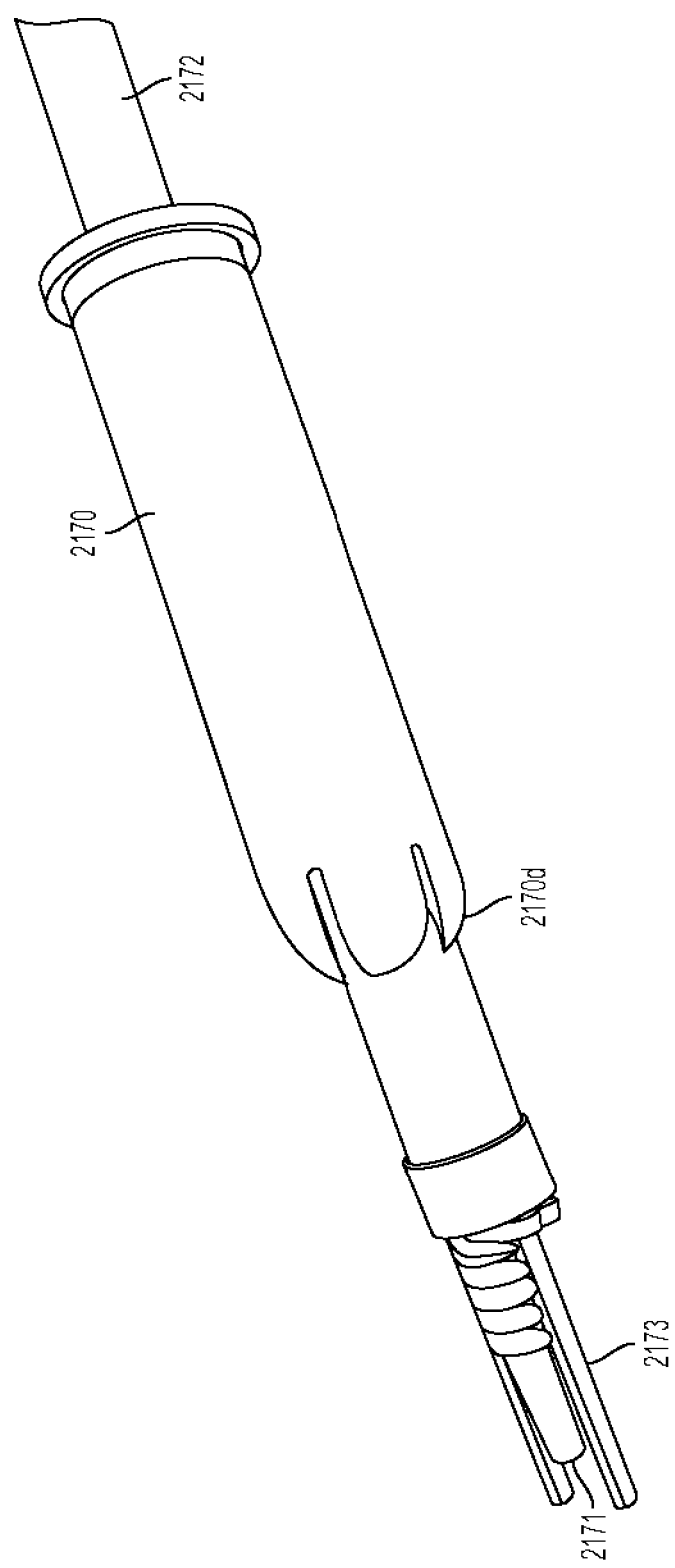
FIG. 31 is another perspective view of the assembly of FIG. 30 showing the sheath protector retracted further relative to the sheath.

In use, as shown in FIGS. 30 and 31, the sheath 2171 and the inserter 2172 with a fork 2173 can be advanced through the distal end of the sheath protector 2170 for allowing plunging of the sheath into a bone hole. FIG. 31 shows the sheath 2171 and the sheath inserter 2172 including the fork and the shaft extending beyond the distal tip of the sheath protector 2170. As noted above, the distal tip 2170d of the sheath protector 2170 can be configured to assist the distal penetration of the sheath 2171 and inserter 2172 with fork 2173 through skin. The sheath protector 2170 can be designed with slits to allow the distal tip 2170d to remain closed during insertion thus preventing the forks or sheath from catching on tissue, and once inserted through tissue to flare open upon distal movement.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A tendon anchoring system, comprising:
   an outer shaft having an inner lumen extending therethrough and a sheath alignment protrusion formed on a distal end thereof;
   an inner shaft disposed within the outer shaft and having first and second prongs formed on a distal end thereof, the prongs being movable between an extended position in which the prongs extend distally beyond the distal end of the outer shaft, and a retracted position in which the prongs are retracted into the distal end of the outer shaft, the prongs extending along opposed sides of the sheath alignment protrusion on the outer shaft;
   a handle assembly coupled to a proximal end of each of the first and second shafts.

2. The tendon anchoring system of claim 1, wherein the sheath alignment protrusion has a generally conical shape.

3. The tendon anchoring system of claim 2, wherein the sheath alignment protrusion includes first and second opposed cut-outs formed therein and configured to receive the first and second prongs of the inner shaft.

4. The tendon anchoring system of claim 1, wherein the distal end of the outer shaft is closed with an elongate slot formed therein for receiving the first and second prongs therethrough.

5. A method for anchoring a tendon to bone, comprising:
   manipulating an inserter tool to insert a sheath coupled to a distal end of the inserter tool through tissue, the sheath having a guidewire mated thereto and extending through the inserter tool;
   positioning a tendon between a pair of prongs on a distal end of the inserter tool, and manipulating the inserter tool to advance the sheath, with the tendon between the prongs, into a bone hole, wherein a locking mechanism on a handle assembly of the inserter tool maintains the guidewire and the prongs in a locked position relative to one another;
   moving the locking mechanism on the handle assembly to an unlocked position and manipulating the handle assembly to retract the prongs relative to the guidewire; and
   removing the inserter tool such that the sheath with the guidewire mated thereto remains in the bone hole.

6. The method of claim 5, wherein the inserter tool includes first and second shafts, and wherein the prongs are formed on the first shaft, and manipulating the handle assembly to retract the prongs relative to the guidewire comprises moving the first shaft relative to the second shaft.

7. The method of claim 6, wherein the locking mechanism extends between a handle on the first shaft and a handle on the second shaft to block movement of the first and second shafts relative to one another when the locking mechanism is in a locked position.

8. The method of claim 6, wherein the first shaft includes an actuator coupled to a proximal end thereof, and wherein the locking mechanism prevents movement of the actuator when in a locked position, and the locking mechanism releases the actuator when it is moved to the unlocked position.

* * * * *